(12) United States Patent
Hill et al.

(10) Patent No.: US 11,564,674 B2
(45) Date of Patent: Jan. 31, 2023

(54) LATERAL ACCESS SYSTEM AND METHOD OF USE

(71) Applicant: K2M, Inc., Leesburg, VA (US)

(72) Inventors: Clint Hill, Paducah, KY (US); Sanjay Khurana, Manhattan Beach, CA (US); Darren Lebl, Greenwich, CT (US); Pierce Dalton Nunley, Shreveport, LA (US); K. Brandon Strenge, Paducah, KY (US); John I. Williams, Fort Wayne, IN (US); Ryan Den Haese, Clarence Center, NY (US); Alexander Horia Artaki, Washington, DC (US); Robert J. Tokash, Stephens City, VA (US); Eric Rodriguez, Purcellville, VA (US); Kaitlin Elizabeth Anne McClymont, Reston, VA (US); Nicholas Padovani, Arlington, VA (US); Daniel Genovese, Great Falls, VA (US); Joshua David Rubin, Reston, VA (US)

(73) Assignee: K2M, Inc., Leesburg, VA (US)

( * ) Notice: Subject to any disclaimer, the term of this patent is extended or adjusted under 35 U.S.C. 154(b) by 169 days.

(21) Appl. No.: 16/832,599

(22) Filed: Mar. 27, 2020

(65) Prior Publication Data
US 2021/0153857 A1 May 27, 2021

Related U.S. Application Data

(60) Provisional application No. 62/941,096, filed on Nov. 27, 2019.

(51) Int. Cl.
*A61B 17/02* (2006.01)

(52) U.S. Cl.
CPC ........ *A61B 17/0206* (2013.01); *A61B 17/025* (2013.01); *A61B 2017/0256* (2013.01)

(58) Field of Classification Search
CPC .............. A61B 17/0206; A61B 17/025; A61B 2017/00367; A61B 2017/0256
See application file for complete search history.

(56) References Cited

U.S. PATENT DOCUMENTS

| 380,745 A | 4/1888 | Chamberlin |
| 447,761 A | 3/1891 | Clough |

(Continued)

FOREIGN PATENT DOCUMENTS

| FR | 2807313 A1 | 10/2001 |
| WO | 9609013 A1 | 3/1996 |

(Continued)

OTHER PUBLICATIONS

Extended European Search Report including Written Opinion for EP20210090.5 dated Jun. 15, 2021; 9 pages.

(Continued)

*Primary Examiner* — Samuel S Hanna
(74) *Attorney, Agent, or Firm* — Duane Morris LLP

(57) ABSTRACT

A surgical retractor includes a body portion and first and second retractor arms operatively coupled thereto. The body portion includes a rotatable knob, a first blade holder, and a first blade. The first blade is configured for axial displacement with the first blade holder and angulation relative to the first blade holder about a first axis. The first and second retractor arms include respective second and third blades detachably secured thereto. The first and second retractor arms are transitionable between an approximated configuration and a spaced apart configuration. The second and third (Continued)

blades are configured to angulate about respective second and third axes that are defined by the respective first and second retractor arms.

15 Claims, 33 Drawing Sheets

(56) References Cited

U.S. PATENT DOCUMENTS

| | | |
|---|---|---|
| 832,201 A | 10/1906 | Fistler |
| 1,157,202 A | 10/1915 | Bates et al. |
| 1,428,653 A | 9/1922 | Nick |
| 1,618,261 A | 2/1927 | Arbogast |
| 1,827,497 A | 10/1931 | Varney |
| 1,839,726 A | 1/1932 | Arnold |
| 1,863,057 A | 6/1932 | Innes |
| 1,944,009 A | 1/1934 | Homer |
| 2,313,164 A | 3/1943 | Nelson |
| 2,586,488 A | 2/1952 | Smith |
| 2,812,758 A | 11/1957 | Blumenschein |
| 2,854,983 A | 10/1958 | Baskin |
| 3,070,088 A | 12/1962 | Brahos |
| 3,087,486 A | 4/1963 | Kilpatrick |
| 3,221,743 A | 12/1965 | Thompson et al. |
| 3,394,700 A | 7/1968 | Yamamoto |
| 3,397,699 A | 8/1968 | Kohl |
| 3,417,746 A | 12/1968 | Moore et al. |
| 3,509,883 A | 5/1970 | Dibelius |
| 3,522,799 A | 8/1970 | Gauthier |
| 3,731,673 A | 5/1973 | Halloran |
| 3,749,088 A | 7/1973 | Kohlmann |
| 3,770,342 A | 11/1973 | Dudragne |
| 3,782,370 A | 1/1974 | McDonald |
| 3,788,318 A | 1/1974 | Kim et al. |
| 3,789,852 A | 2/1974 | Kim et al. |
| 3,796,214 A | 3/1974 | Davis |
| 3,807,393 A | 4/1974 | McDonald |
| 3,944,341 A | 3/1976 | Pomerantzeff |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,141,364 A | 2/1979 | Schultze |
| 4,226,228 A | 10/1980 | Shin et al. |
| 4,254,763 A | 3/1981 | McCready et al. |
| 4,312,353 A | 1/1982 | Shahbabian |
| 4,337,763 A | 7/1982 | Petrassevich |
| 4,545,374 A | 10/1985 | Jacobson |
| 4,589,868 A | 5/1986 | Dretler |
| 4,616,635 A | 10/1986 | Caspar et al. |
| 4,617,916 A | 10/1986 | LeVahn et al. |
| 4,716,901 A | 1/1988 | Jackson et al. |
| 4,718,151 A | 1/1988 | LeVahn et al. |
| 4,739,762 A | 4/1988 | Palmaz |
| 4,779,611 A | 10/1988 | Grooters et al. |
| 4,813,401 A | 3/1989 | Grieshaber |
| 4,817,587 A | 4/1989 | Janese |
| 4,896,669 A | 1/1990 | Bhate et al. |
| 4,949,707 A | 8/1990 | LeVahn et al. |
| 4,971,037 A | 11/1990 | Pelta |
| 4,971,038 A | 11/1990 | Farley |
| 5,032,113 A | 7/1991 | Burns |
| 5,052,373 A | 10/1991 | Michelson |
| 5,092,314 A | 3/1992 | Zeitels |
| 5,116,318 A | 5/1992 | Hillstead |
| 5,139,511 A | 8/1992 | Gill et al. |
| 5,183,464 A | 2/1993 | Dubrul et al. |
| 5,312,417 A | 5/1994 | Wilk |
| 5,320,611 A | 6/1994 | Bonutti et al. |
| 5,351,679 A | 10/1994 | Mayzels et al. |
| 5,377,667 A | 1/1995 | Patton et al. |
| 5,383,889 A | 1/1995 | Warner et al. |
| 5,391,156 A | 2/1995 | Hildwein et al. |
| 5,391,178 A | 2/1995 | Yapor |
| 5,425,730 A | 6/1995 | Luloh |
| 5,431,676 A | 7/1995 | Dubrul et al. |
| 5,452,732 A | 9/1995 | Bircoll |
| 5,460,170 A | 10/1995 | Hammerslag |
| 5,474,057 A | 12/1995 | Makower et al. |
| 5,496,345 A | 3/1996 | Kieturakis et al. |
| 5,505,690 A | 4/1996 | Patton |
| 5,512,038 A | 4/1996 | O'Neal et al. |
| 5,514,153 A | 5/1996 | Bonutti |
| 5,520,611 A | 5/1996 | Rao et al. |
| 5,522,790 A | 6/1996 | Moll et al. |
| 5,580,344 A | 12/1996 | Hasson |
| 5,607,441 A | 3/1997 | Sierocuk et al. |
| 5,653,726 A | 8/1997 | Kieturakis |
| 5,678,572 A | 10/1997 | Shaw et al. |
| 5,685,826 A | 11/1997 | Bonutti |
| 5,688,223 A | 11/1997 | Rosendahl |
| 5,702,417 A | 12/1997 | Hermann |
| 5,707,362 A | 1/1998 | Yoon |
| 5,728,046 A | 3/1998 | Mayer et al. |
| 5,755,661 A | 5/1998 | Schwartzman |
| 5,772,661 A | 6/1998 | Michelson |
| 5,772,681 A | 6/1998 | Leoni |
| 5,782,854 A | 7/1998 | Hermann |
| 5,827,318 A | 10/1998 | Bonutti |
| 5,827,319 A | 10/1998 | Carlson et al. |
| 5,830,191 A | 11/1998 | Hildwein et al. |
| 5,860,997 A | 1/1999 | Bonutti |
| 5,865,802 A | 2/1999 | Yoon et al. |
| 5,888,196 A | 3/1999 | Bonutti |
| 5,888,197 A | 3/1999 | Mulac et al. |
| 5,893,866 A | 4/1999 | Hermann et al. |
| 5,897,087 A | 4/1999 | Farley |
| 5,916,151 A | 6/1999 | Charters |
| 5,919,128 A | 7/1999 | Fitch |
| 5,928,139 A | 7/1999 | Koros et al. |
| 5,941,777 A | 8/1999 | Moser et al. |
| 5,944,658 A | 8/1999 | Koros et al. |
| 5,944,734 A | 8/1999 | Hermann et al. |
| 5,954,739 A | 9/1999 | Bonutti |
| 5,957,832 A | 9/1999 | Taylor et al. |
| 5,961,499 A | 10/1999 | Bonutti et al. |
| 5,967,970 A | 10/1999 | Cowan et al. |
| 5,993,472 A | 11/1999 | Hermann et al. |
| 6,004,337 A | 12/1999 | Kieturakis et al. |
| 6,004,340 A | 12/1999 | Hermann et al. |
| 6,022,340 A | 2/2000 | Sepetka et al. |
| 6,027,518 A | 2/2000 | Gaber |
| 6,032,671 A | 3/2000 | Mollenauer et al. |
| 6,036,689 A | 3/2000 | Tu et al. |
| 6,074,343 A | 6/2000 | Nathanson et al. |
| 6,079,761 A | 6/2000 | Sadeck |
| 6,080,174 A | 6/2000 | Dubrul et al. |
| 6,083,154 A | 7/2000 | Liu et al. |
| 6,093,173 A | 7/2000 | Balceta et al. |
| 6,102,928 A | 8/2000 | Bonutti |
| 6,139,493 A | 10/2000 | Koros et al. |
| 6,171,299 B1 | 1/2001 | Bonutti |
| 6,187,023 B1 | 2/2001 | Bonutti |
| 6,206,826 B1 | 3/2001 | Mathews et al. |
| 6,206,886 B1 | 3/2001 | Bennett |
| 6,234,961 B1 | 5/2001 | Gray |
| 6,235,043 B1 | 5/2001 | Reiley et al. |
| 6,258,089 B1 | 7/2001 | Campbell et al. |
| 6,267,424 B1 | 7/2001 | Gillette |
| 6,277,136 B1 | 8/2001 | Bonutti |
| 6,312,443 B1 | 11/2001 | Stone |
| 6,322,500 B1 | 11/2001 | Sikora et al. |
| 6,325,812 B1 | 12/2001 | Dubrul et al. |
| 6,338,730 B1 | 1/2002 | Bonutti et al. |
| 6,354,995 B1 | 3/2002 | Hoftman et al. |
| 6,387,095 B1 | 5/2002 | Kennett et al. |
| 6,431,025 B1 | 8/2002 | Koros et al. |
| 6,436,119 B1 | 8/2002 | Erb et al. |
| 6,464,634 B1 | 10/2002 | Fraser |
| 6,464,697 B1 | 10/2002 | Edwards et al. |
| 6,466,817 B1 | 10/2002 | Kaula et al. |
| 6,468,205 B1 | 10/2002 | Mollenauer et al. |
| 6,494,893 B2 | 12/2002 | Dubrul et al. |
| 6,511,423 B2 | 1/2003 | Farley |

(56) References Cited

U.S. PATENT DOCUMENTS

| | | |
|---|---|---|
| 6,564,078 B1 | 5/2003 | Marino et al. |
| 6,569,182 B1 | 5/2003 | Balceta et al. |
| 6,592,602 B1 | 7/2003 | Peartree et al. |
| 6,602,190 B2 | 8/2003 | Dobrovolny |
| 6,616,605 B2 | 9/2003 | Wright et al. |
| 6,632,234 B2 | 10/2003 | Kieturakis et al. |
| 6,632,235 B2 | 10/2003 | Weikel et al. |
| 6,689,152 B2 | 2/2004 | Balceta et al. |
| 6,692,462 B2 | 2/2004 | Mackenzie et al. |
| 6,760,616 B2 | 7/2004 | Hoey et al. |
| 6,814,715 B2 | 11/2004 | Bonutti et al. |
| 6,846,287 B2 | 1/2005 | Bonadio et al. |
| 6,849,064 B2 | 2/2005 | Hamada |
| 6,866,676 B2 | 3/2005 | Kieturakis et al. |
| 6,869,398 B2 | 3/2005 | Obenchain et al. |
| 6,921,364 B2 | 7/2005 | Mollenauer et al. |
| 6,945,933 B2 | 9/2005 | Branch et al. |
| 6,948,751 B2 | 9/2005 | Wooten et al. |
| 7,050,848 B2 | 5/2006 | Hoey et al. |
| 7,056,321 B2 | 6/2006 | Pagliuca et al. |
| 7,079,883 B2 | 7/2006 | Marino et al. |
| 7,144,368 B2 | 12/2006 | Larson et al. |
| 7,150,714 B2 | 12/2006 | Myles |
| 7,177,677 B2 | 2/2007 | Kaula et al. |
| 7,195,592 B2 | 3/2007 | Ravikumar et al. |
| 7,207,949 B2 | 4/2007 | Miles et al. |
| 7,211,098 B2 | 5/2007 | Dallara et al. |
| 7,217,273 B2 | 5/2007 | Bonutti |
| 7,223,233 B2 | 5/2007 | Branch et al. |
| 7,235,064 B2 | 6/2007 | Hopper et al. |
| 7,261,688 B2 | 8/2007 | Smith et al. |
| 7,294,136 B2 | 11/2007 | Dubrul et al. |
| 7,311,719 B2 | 12/2007 | Bonutti |
| 7,326,226 B2 | 2/2008 | Root et al. |
| 7,329,268 B2 | 2/2008 | Van Nguyen et al. |
| 7,344,495 B2 | 3/2008 | Ravikumar et al. |
| 7,374,534 B2 | 5/2008 | Dalton |
| 7,390,298 B2 | 6/2008 | Chu |
| 7,396,329 B2 | 7/2008 | Nakao |
| 7,407,483 B2 | 8/2008 | Perez-Cruet et al. |
| 7,435,219 B2 | 10/2008 | Kim |
| 7,455,639 B2 | 11/2008 | Ritland |
| 7,458,933 B2 | 12/2008 | LeVahn et al. |
| 7,470,236 B1 | 12/2008 | Kelleher et al. |
| 7,473,222 B2 | 1/2009 | Dewey et al. |
| 7,476,232 B2 | 1/2009 | Deal |
| 7,488,337 B2 | 2/2009 | Saab et al. |
| 7,491,168 B2 | 2/2009 | Raymond et al. |
| 7,510,524 B2 | 3/2009 | Vayser et al. |
| 7,513,869 B2 | 4/2009 | Branch et al. |
| 7,522,953 B2 | 4/2009 | Kaula et al. |
| 7,556,600 B2 | 7/2009 | Landry et al. |
| 7,582,058 B1 | 9/2009 | Miles et al. |
| 7,594,888 B2 | 9/2009 | Raymond et al. |
| 7,641,664 B2 | 1/2010 | Pagano |
| 7,645,232 B2 | 1/2010 | Shluzas |
| 7,682,378 B2 | 3/2010 | Truckai et al. |
| 7,683,565 B2 | 3/2010 | Quaid et al. |
| 7,686,492 B2 | 3/2010 | Vayser et al. |
| 7,691,057 B2 | 4/2010 | Miles et al. |
| 7,691,657 B2 | 4/2010 | Lee |
| 7,693,562 B2 | 4/2010 | Marino et al. |
| 7,704,267 B2 | 4/2010 | Tessmer |
| 7,744,612 B2 | 6/2010 | Blain |
| 7,747,311 B2 | 6/2010 | Quaid, III |
| 7,758,501 B2 | 7/2010 | Frasier et al. |
| 7,780,594 B2 | 8/2010 | Hutton |
| 7,785,253 B1 | 8/2010 | Arambula et al. |
| 7,811,230 B2 | 10/2010 | Hsueh et al. |
| 7,819,801 B2 | 10/2010 | Miles et al. |
| 7,850,608 B2 | 12/2010 | Hamada |
| 7,874,982 B2 | 1/2011 | Selover et al. |
| 7,883,522 B2 | 2/2011 | Hamada |
| 7,887,482 B2 | 2/2011 | Hamada |
| 7,891,801 B2 | 2/2011 | Nakajima |
| 7,892,173 B2 | 2/2011 | Miles et al. |
| 7,905,840 B2 | 3/2011 | Pimenta et al. |
| 7,909,761 B2 | 3/2011 | Banchieri et al. |
| 7,909,832 B2 | 3/2011 | Michelson |
| 7,918,891 B1 | 4/2011 | Curran et al. |
| 7,920,922 B2 | 4/2011 | Gharib et al. |
| 7,931,589 B2 | 4/2011 | Cohen et al. |
| 7,935,051 B2 | 5/2011 | Miles et al. |
| 7,935,053 B2 | 5/2011 | Karpowicz et al. |
| 7,946,982 B2 | 5/2011 | Hamada |
| 7,962,191 B2 | 6/2011 | Marino et al. |
| 7,963,927 B2 | 6/2011 | Kelleher et al. |
| 7,976,463 B2 | 7/2011 | Dewey et al. |
| 7,981,029 B2 | 7/2011 | Branch et al. |
| 7,985,179 B2 | 7/2011 | Gephart et al. |
| 3,000,782 A1 | 8/2011 | Gharib et al. |
| 3,005,535 A1 | 8/2011 | Gharib et al. |
| 3,010,180 A1 | 8/2011 | Quaid et al. |
| 7,988,623 B2 | 8/2011 | Pagliuca et al. |
| 7,988,624 B2 | 8/2011 | Smith et al. |
| 7,991,463 B2 | 8/2011 | Kelleher et al. |
| 8,016,767 B2 | 9/2011 | Miles et al. |
| 8,027,716 B2 | 9/2011 | Gharib et al. |
| 8,050,769 B2 | 11/2011 | Gharib et al. |
| 8,055,349 B2 | 11/2011 | Gharib et al. |
| 8,062,217 B2 | 11/2011 | Boucher et al. |
| 8,062,303 B2 | 11/2011 | Berry et al. |
| 8,068,912 B2 | 11/2011 | Kaula et al. |
| D652,519 S | 1/2012 | Miles et al. |
| D652,921 S | 1/2012 | Miles et al. |
| D652,922 S | 1/2012 | Miles et al. |
| 8,090,436 B2 | 1/2012 | Hoey et al. |
| 8,095,200 B2 | 1/2012 | Quaid, III |
| 8,105,236 B2 | 1/2012 | Malandain et al. |
| 8,114,019 B2 | 2/2012 | Miles et al. |
| 8,114,161 B2 | 2/2012 | Evans et al. |
| 8,114,689 B2 | 2/2012 | Kang et al. |
| 8,133,173 B2 | 3/2012 | Miles et al. |
| 8,137,284 B2 | 3/2012 | Miles et al. |
| 8,152,721 B2 | 4/2012 | Michaeli et al. |
| 8,157,728 B2 | 4/2012 | Danna et al. |
| 8,165,653 B2 | 4/2012 | Marino et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,187,334 B2 | 5/2012 | Curran et al. |
| 8,192,356 B2 | 6/2012 | Miles et al. |
| 8,192,357 B2 | 6/2012 | Miles et al. |
| 8,206,293 B2 | 6/2012 | Reglos et al. |
| D666,292 S | 8/2012 | Miles et al. |
| D666,293 S | 8/2012 | Miles et al. |
| D666,294 S | 8/2012 | Miles et al. |
| 8,244,343 B2 | 8/2012 | Gharib et al. |
| 8,246,686 B1 | 8/2012 | Curran et al. |
| 8,265,744 B2 | 9/2012 | Gharib et al. |
| 8,287,522 B2 | 10/2012 | Moses et al. |
| 8,298,139 B2 | 10/2012 | Hamada |
| 8,303,498 B2 | 11/2012 | Miles et al. |
| 8,303,499 B2 | 11/2012 | Hamada |
| 8,303,515 B2 | 11/2012 | Miles et al. |
| 8,317,693 B2 | 11/2012 | Grey et al. |
| 8,323,185 B2 | 12/2012 | Perez-Cruet et al. |
| 8,337,410 B2 | 12/2012 | Kelleher et al. |
| 8,343,046 B2 | 1/2013 | Miles et al. |
| 8,343,065 B2 | 1/2013 | Bartol et al. |
| 8,343,079 B2 | 1/2013 | Bartol et al. |
| 8,348,837 B2 | 1/2013 | Wenchell |
| 8,353,826 B2 | 1/2013 | Weiman |
| 8,355,780 B2 | 1/2013 | Miles et al. |
| 8,361,156 B2 | 1/2013 | Curran et al. |
| 8,376,937 B2 | 2/2013 | Xia et al. |
| 8,388,527 B2 | 3/2013 | Miles et al. |
| 8,403,841 B2 | 3/2013 | Miles et al. |
| 8,409,089 B2 | 4/2013 | Michaeli et al. |
| 8,430,813 B2 | 4/2013 | Selover et al. |
| 8,439,832 B2 | 5/2013 | Miles et al. |
| 8,449,463 B2 | 5/2013 | Nunley et al. |
| 8,454,504 B2 | 6/2013 | Michaeli et al. |
| 8,480,704 B2 | 7/2013 | Heiges et al. |

(56) References Cited

U.S. PATENT DOCUMENTS

| | | |
|---|---|---|
| 8,489,170 B2 | 7/2013 | Marino et al. |
| 8,491,471 B2 | 7/2013 | Deshmukh et al. |
| 8,500,634 B2 | 8/2013 | Miles et al. |
| 8,512,235 B2 | 8/2013 | Miles et al. |
| 8,517,954 B2 | 8/2013 | Bartol et al. |
| 8,523,767 B2 | 9/2013 | DeRidder et al. |
| 8,523,768 B2 | 9/2013 | Miles et al. |
| 8,545,531 B2 | 10/2013 | Geist et al. |
| 8,548,579 B2 | 10/2013 | Gharib et al. |
| 8,550,994 B2 | 10/2013 | Miles et al. |
| 8,556,808 B2 | 10/2013 | Miles et al. |
| 8,562,521 B2 | 10/2013 | Miles et al. |
| 8,562,539 B2 | 10/2013 | Marino |
| 8,568,317 B1 | 10/2013 | Gharib et al. |
| 8,571,628 B2 | 10/2013 | Kang et al. |
| 8,574,301 B2 | 11/2013 | Curran et al. |
| 8,585,762 B2 | 11/2013 | Hall |
| 8,591,432 B2 | 11/2013 | Pimenta et al. |
| 8,591,567 B2 | 11/2013 | Chau et al. |
| 8,602,982 B2 | 12/2013 | Miles et al. |
| 8,602,984 B2 | 12/2013 | Raymond et al. |
| 8,608,652 B2 | 12/2013 | Voegele et al. |
| 8,608,804 B2 | 12/2013 | Curran et al. |
| 8,622,897 B2 | 1/2014 | Raymond et al. |
| 8,628,469 B2 | 1/2014 | Miles et al. |
| 8,634,904 B2 | 1/2014 | Kaula et al. |
| 8,635,725 B2 | 1/2014 | Tannoury et al. |
| 8,636,656 B2 | 1/2014 | Nichter et al. |
| 8,636,657 B2 | 1/2014 | Hamada |
| 8,641,638 B2 | 2/2014 | Kelleher et al. |
| 8,663,100 B2 | 3/2014 | Miles et al. |
| 8,663,102 B2 | 3/2014 | Michaeli et al. |
| 8,672,840 B2 | 3/2014 | Miles et al. |
| 8,679,006 B2 | 3/2014 | Miles et al. |
| 8,685,105 B2 | 4/2014 | Curran et al. |
| 8,696,559 B2 | 4/2014 | Miles et al. |
| 8,702,600 B2 | 4/2014 | Perrow |
| 8,708,899 B2 | 4/2014 | Miles et al. |
| 8,738,123 B2 | 5/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,758,236 B2 | 6/2014 | Albrecht et al. |
| 8,764,649 B2 | 7/2014 | Miles et al. |
| 8,768,450 B2 | 7/2014 | Gharib et al. |
| 8,795,167 B2 | 8/2014 | Ainsworth et al. |
| 8,801,608 B2 | 8/2014 | Hardenbrook |
| 8,808,172 B2 | 8/2014 | Manzanares |
| 8,812,116 B2 | 8/2014 | Kaula et al. |
| 8,814,940 B2 | 8/2014 | Curran et al. |
| 8,821,394 B2 | 9/2014 | Hawkins et al. |
| 8,821,396 B1 | 9/2014 | Miles et al. |
| 8,852,089 B2 | 10/2014 | Blackwell et al. |
| 8,855,822 B2 | 10/2014 | Bartol et al. |
| 8,870,760 B2 | 10/2014 | Heiges et al. |
| 8,876,687 B2 | 11/2014 | Jones et al. |
| 8,882,661 B2 | 11/2014 | Hutton et al. |
| 8,882,679 B2 | 11/2014 | Bartol et al. |
| 8,892,259 B2 | 11/2014 | Bartol et al. |
| 8,894,574 B2 | 11/2014 | Ellman |
| 8,900,137 B1 | 12/2014 | Lovell et al. |
| 8,911,364 B2 | 12/2014 | Feigenwinter et al. |
| 8,915,846 B2 | 12/2014 | Miles et al. |
| 8,932,360 B2 | 1/2015 | Womble et al. |
| 8,942,797 B2 | 1/2015 | Bartol et al. |
| 8,942,801 B2 | 1/2015 | Miles et al. |
| 8,945,004 B2 | 2/2015 | Miles et al. |
| 8,956,283 B2 | 2/2015 | Miles et al. |
| 8,958,869 B2 | 2/2015 | Kelleher et al. |
| 8,968,363 B2 | 3/2015 | Weiman et al. |
| 8,977,352 B2 | 3/2015 | Gharib et al. |
| 8,979,767 B2 | 3/2015 | Bartol et al. |
| 8,983,593 B2 | 3/2015 | Bartol et al. |
| 8,986,344 B2 | 3/2015 | Sandhu |
| 8,992,425 B2 | 3/2015 | Karpowicz et al. |
| 8,992,558 B2 | 3/2015 | Stone et al. |
| 9,014,776 B2 | 4/2015 | Marino et al. |
| 9,037,250 B2 | 5/2015 | Kaula et al. |
| 9,039,630 B2 | 5/2015 | Bartol et al. |
| 9,044,280 B1 | 6/2015 | Arambula et al. |
| 9,050,146 B2 | 6/2015 | Woolley et al. |
| 9,060,757 B2 | 6/2015 | Lawson et al. |
| 9,066,701 B1 | 6/2015 | Finley et al. |
| 9,084,550 B1 | 7/2015 | Bartol et al. |
| 9,095,301 B2 | 8/2015 | Hamada |
| 9,113,854 B2 | 8/2015 | Ellman |
| 9,125,587 B2 | 9/2015 | Hawkins et al. |
| 9,138,137 B2 | 9/2015 | Deshmukh et al. |
| 9,138,217 B2 | 9/2015 | Smith et al. |
| 9,180,021 B2 | 11/2015 | Curran et al. |
| 9,204,871 B2 | 12/2015 | Miles et al. |
| 9,206,947 B2 | 12/2015 | Baumgartner et al. |
| 9,220,491 B2 | 12/2015 | Nunley et al. |
| 9,259,144 B2 | 2/2016 | Smith et al. |
| 9,265,493 B2 | 2/2016 | Miles et al. |
| 9,271,709 B2 | 3/2016 | Grey et al. |
| 9,271,711 B2 | 3/2016 | Hawkins et al. |
| 9,301,711 B2 | 4/2016 | Bartol et al. |
| 9,301,743 B2 | 4/2016 | Miles et al. |
| 9,314,152 B2 | 4/2016 | Pimenta et al. |
| 9,320,506 B2 | 4/2016 | Bertagnoli et al. |
| 9,339,263 B2 | 5/2016 | Fenn et al. |
| 9,351,718 B1 | 5/2016 | Arambula et al. |
| 9,380,932 B1 | 7/2016 | Lynn et al. |
| 9,386,916 B2 | 7/2016 | Predick et al. |
| 9,387,009 B2 | 7/2016 | Fatone et al. |
| 9,408,598 B1 | 8/2016 | Fantini et al. |
| 9,429,746 B2 | 8/2016 | Vayser et al. |
| 9,458,935 B2 | 10/2016 | Fricke et al. |
| 9,480,855 B2 | 11/2016 | DiMauro et al. |
| 9,486,133 B2 | 11/2016 | Coleman et al. |
| 9,498,200 B2 | 11/2016 | Pfabe et al. |
| 9,554,789 B2 | 1/2017 | Overes et al. |
| 9,572,560 B2 | 2/2017 | Mast et al. |
| 9,610,130 B2 | 4/2017 | Vayser et al. |
| 9,615,818 B2 | 4/2017 | Baudouin et al. |
| 9,622,732 B2 | 4/2017 | Martinelli et al. |
| 9,636,097 B2 | 5/2017 | Bass |
| 9,642,607 B2 | 5/2017 | Bootwala |
| 9,649,101 B2 | 5/2017 | Karpowicz et al. |
| 9,655,505 B1 | 5/2017 | Gharib et al. |
| 9,693,761 B2 | 7/2017 | Fedorov et al. |
| 9,782,158 B2 | 10/2017 | Nunley et al. |
| 9,795,370 B2 | 10/2017 | O'Connell et al. |
| 9,808,231 B2 | 11/2017 | Miraki et al. |
| 9,808,232 B2 | 11/2017 | Heiman et al. |
| 9,848,863 B2 | 12/2017 | Cryder et al. |
| 9,968,347 B2 | 5/2018 | Hutton et al. |
| 10,004,488 B2 | 6/2018 | Simonson |
| 10,046,149 B2 | 8/2018 | Bootwala |
| 10,172,515 B2 | 1/2019 | Coleman et al. |
| 10,188,376 B2 | 1/2019 | Miraki et al. |
| 2001/0039430 A1 | 11/2001 | Dubrul et al. |
| 2002/0193822 A1 | 12/2002 | Hung et al. |
| 2003/0018352 A1 | 1/2003 | Mollenauer et al. |
| 2003/0023259 A1 | 1/2003 | Dubrul et al. |
| 2003/0181939 A1 | 9/2003 | Bonutti |
| 2003/0191371 A1 | 10/2003 | Smith et al. |
| 2003/0195405 A1 | 10/2003 | Marino et al. |
| 2003/0225432 A1 | 12/2003 | Baptiste et al. |
| 2003/0225433 A1 | 12/2003 | Nakao |
| 2003/0229273 A1 | 12/2003 | Mulac et al. |
| 2003/0233115 A1 | 12/2003 | Eversull et al. |
| 2004/0087833 A1 | 5/2004 | Bauer et al. |
| 2004/0236186 A1 | 11/2004 | Chu |
| 2004/0243158 A1 | 12/2004 | Konstantino et al. |
| 2004/0243167 A1 | 12/2004 | Tanaka et al. |
| 2005/0119531 A1 | 6/2005 | Sharratt |
| 2005/0124937 A1 | 6/2005 | Kick et al. |
| 2005/0182436 A1 | 8/2005 | Chopra |
| 2005/0234304 A1 | 10/2005 | Dewey et al. |
| 2005/0234493 A1 | 10/2005 | Carr et al. |
| 2006/0004398 A1 | 1/2006 | Binder et al. |
| 2006/0052750 A1 | 3/2006 | Lenker et al. |

(56) References Cited

U.S. PATENT DOCUMENTS

| | | |
|---|---|---|
| 2006/0135852 A1 | 6/2006 | Koros et al. |
| 2006/0135981 A1 | 6/2006 | Lenker et al. |
| 2006/0135987 A1 | 6/2006 | Jones et al. |
| 2006/0206008 A1 | 9/2006 | Dalton |
| 2006/0206009 A1 | 9/2006 | Von Wald et al. |
| 2006/0224044 A1 | 10/2006 | Marchek et al. |
| 2006/0224045 A1 | 10/2006 | Whipple et al. |
| 2006/0224078 A1 | 10/2006 | Hoey et al. |
| 2006/0258951 A1 | 11/2006 | Bleich et al. |
| 2006/0287574 A1 | 12/2006 | Chin |
| 2007/0010716 A1 | 1/2007 | Malandain et al. |
| 2007/0032703 A1 | 2/2007 | Sankaran et al. |
| 2007/0049962 A1 | 3/2007 | Marino et al. |
| 2007/0060939 A1 | 3/2007 | Lancial et al. |
| 2007/0168043 A1 | 7/2007 | Ferree |
| 2007/0208366 A1 | 9/2007 | Pellegrino et al. |
| 2007/0213591 A1 | 9/2007 | Aizenfeld et al. |
| 2007/0219416 A1 | 9/2007 | Perez-Cruet et al. |
| 2007/0239159 A1 | 10/2007 | Altarac et al. |
| 2007/0270623 A1 | 11/2007 | Merrill |
| 2007/0270653 A1 | 11/2007 | Vayser et al. |
| 2008/0058606 A1 | 3/2008 | Miles et al. |
| 2008/0064945 A1 | 3/2008 | Marino et al. |
| 2008/0065135 A1 | 3/2008 | Marino et al. |
| 2008/0065140 A1 | 3/2008 | Bonutti |
| 2008/0065144 A1 | 3/2008 | Marino et al. |
| 2008/0065178 A1 | 3/2008 | Kelleher et al. |
| 2008/0071191 A1 | 3/2008 | Kelleher et al. |
| 2008/0103519 A1 | 5/2008 | Bonutti |
| 2008/0109026 A1 | 5/2008 | Kassam |
| 2008/0132764 A1 | 6/2008 | Hamada |
| 2008/0147109 A1 | 6/2008 | Kambin et al. |
| 2008/0183204 A1 | 7/2008 | Greenhalgh et al. |
| 2008/0215081 A1 | 9/2008 | Hsueh et al. |
| 2008/0221586 A1 | 9/2008 | Garcia-Bengochea et al. |
| 2008/0255563 A1 | 10/2008 | Farr et al. |
| 2008/0319268 A1 | 12/2008 | Michaeli et al. |
| 2008/0319432 A1 | 12/2008 | Ely et al. |
| 2009/0024158 A1 | 1/2009 | Viker |
| 2009/0036744 A1 | 2/2009 | Vayser |
| 2009/0036746 A1 | 2/2009 | Blackwell et al. |
| 2009/0062871 A1 | 3/2009 | Chin et al. |
| 2009/0149716 A1 | 6/2009 | Diao et al. |
| 2009/0171284 A1 | 7/2009 | Burke et al. |
| 2010/0041955 A1 | 2/2010 | Grey et al. |
| 2010/0160947 A1 | 6/2010 | Akyuz et al. |
| 2010/0178100 A1 | 7/2010 | Fricke et al. |
| 2010/0180906 A1 | 7/2010 | Marozsan et al. |
| 2010/0241129 A1 | 9/2010 | Markey et al. |
| 2011/0208005 A1 | 8/2011 | Michaeli et al. |
| 2011/0224497 A1* | 9/2011 | Weiman ............ A61B 17/02 |
| | | 600/231 |
| 2011/0237898 A1 | 9/2011 | Stone et al. |
| 2011/0313312 A1 | 12/2011 | Hoey et al. |
| 2012/0010472 A1 | 1/2012 | Spann |
| 2012/0022575 A1 | 1/2012 | Mire et al. |
| 2012/0029382 A1 | 2/2012 | Kelleher et al. |
| 2012/0035730 A1 | 2/2012 | Spann |
| 2012/0041272 A1 | 2/2012 | Dietze, Jr. et al. |
| 2012/0046526 A1 | 2/2012 | Boettner et al. |
| 2012/0101341 A1 | 4/2012 | Malandain et al. |
| 2012/0232349 A1 | 9/2012 | Perrow |
| 2012/0245431 A1* | 9/2012 | Baudouin .......... A61B 17/0206 |
| | | 600/219 |
| 2013/0090680 A1 | 4/2013 | Akyuz et al. |
| 2013/0103103 A1 | 4/2013 | Mire et al. |
| 2013/0123582 A1 | 5/2013 | Xia et al. |
| 2013/0190575 A1 | 7/2013 | Mast et al. |
| 2013/0211202 A1 | 8/2013 | Perez-Cruet et al. |
| 2013/0317303 A1 | 11/2013 | Deshmukh et al. |
| 2014/0039264 A1 | 2/2014 | Heiman |
| 2014/0114135 A1 | 4/2014 | Ellman |
| 2014/0114138 A1 | 4/2014 | Fedorov et al. |
| 2014/0114139 A1 | 4/2014 | Ziolo et al. |
| 2014/0128979 A1 | 5/2014 | Womble et al. |
| 2014/0142420 A1 | 5/2014 | Jackson, III |
| 2014/0148650 A1 | 5/2014 | Miles et al. |
| 2014/0172002 A1 | 6/2014 | Predick |
| 2014/0235950 A1 | 8/2014 | Miles et al. |
| 2014/0257035 A1 | 9/2014 | Blain |
| 2014/0257044 A1 | 9/2014 | Blain et al. |
| 2014/0275801 A1 | 9/2014 | Menchaca et al. |
| 2014/0276869 A1 | 9/2014 | Tatsumi |
| 2014/0288374 A1 | 9/2014 | Miles et al. |
| 2014/0288375 A1 | 9/2014 | Miles et al. |
| 2014/0316212 A1 | 10/2014 | Reimels |
| 2014/0357946 A1 | 12/2014 | Golden et al. |
| 2015/0018623 A1 | 1/2015 | Friedrich et al. |
| 2015/0018625 A1 | 1/2015 | Miraki et al. |
| 2015/0045626 A1 | 2/2015 | Reimels |
| 2015/0051448 A1 | 2/2015 | Hunt et al. |
| 2015/0051506 A1 | 2/2015 | Wybo et al. |
| 2015/0051507 A1 | 2/2015 | Wybo et al. |
| 2015/0080717 A1 | 3/2015 | Ferko |
| 2015/0088029 A1 | 3/2015 | Wybo |
| 2015/0088030 A1 | 3/2015 | Taylor |
| 2015/0105624 A1 | 4/2015 | Martinelli et al. |
| 2015/0112148 A1 | 4/2015 | Bouquet |
| 2015/0119987 A1 | 4/2015 | Davignon et al. |
| 2015/0133734 A1 | 5/2015 | Miles et al. |
| 2015/0150693 A1 | 6/2015 | Gharib et al. |
| 2015/0157227 A1 | 6/2015 | Kelleher et al. |
| 2015/0157228 A1 | 6/2015 | Marino et al. |
| 2015/0164496 A1 | 6/2015 | Karpowicz et al. |
| 2015/0164569 A1 | 6/2015 | Reitblat et al. |
| 2015/0216478 A1 | 8/2015 | Kaula et al. |
| 2015/0230749 A1 | 8/2015 | Gharib et al. |
| 2015/0230787 A1 | 8/2015 | Friedrich et al. |
| 2015/0257784 A1 | 9/2015 | Corbin et al. |
| 2015/0327948 A1 | 11/2015 | Schoepp et al. |
| 2015/0342589 A1 | 12/2015 | Bootwala |
| 2015/0366548 A1 | 12/2015 | Lauchner |
| 2016/0038302 A1 | 2/2016 | Curran et al. |
| 2016/0051242 A1 | 2/2016 | Predick et al. |
| 2016/0081681 A1 | 3/2016 | Waugh et al. |
| 2016/0081682 A1 | 3/2016 | Miles et al. |
| 2016/0120530 A1 | 5/2016 | Miles et al. |
| 2016/0120532 A1 | 5/2016 | Donald |
| 2016/0174958 A1 | 6/2016 | Miles et al. |
| 2016/0174959 A1 | 6/2016 | Miles et al. |
| 2016/0183913 A1 | 6/2016 | Singh et al. |
| 2016/0192921 A1 | 7/2016 | Pimenta et al. |
| 2016/0192922 A1 | 7/2016 | Friedrich et al. |
| 2016/0199193 A1 | 7/2016 | Willis et al. |
| 2016/0242736 A1 | 8/2016 | Freiburg et al. |
| 2016/0278755 A1 | 9/2016 | Stone et al. |
| 2016/0317137 A1 | 11/2016 | Predick et al. |
| 2016/0338795 A1 | 11/2016 | Vayser et al. |
| 2016/0345949 A1 | 12/2016 | Harvey et al. |
| 2016/0361052 A1 | 12/2016 | Reimels |
| 2017/0000562 A1 | 1/2017 | Frank et al. |
| 2017/0007228 A1 | 1/2017 | Costabile |
| 2017/0014118 A1 | 1/2017 | Capote |
| 2017/0014119 A1 | 1/2017 | Capote et al. |
| 2017/0027555 A1 | 2/2017 | Paumier et al. |
| 2017/0065268 A1 | 3/2017 | Sindram |
| 2017/0071589 A1 | 3/2017 | Simonson |
| 2017/0150956 A1 | 6/2017 | Baudouin et al. |
| 2017/0215856 A1 | 8/2017 | Martinelli et al. |
| 2017/0231614 A1 | 8/2017 | Vogel et al. |
| 2017/0340317 A1 | 11/2017 | Fatone et al. |
| 2018/0064450 A1 | 3/2018 | Jackson, III |
| 2018/0333152 A1 | 11/2018 | Heiman |
| 2019/0216570 A1 | 7/2019 | Friedrich et al. |

FOREIGN PATENT DOCUMENTS

| | | |
|---|---|---|
| WO | 9916499 A1 | 4/1999 |
| WO | 2006102085 A2 | 9/2006 |
| WO | 2008039427 A2 | 4/2008 |

(56) References Cited

FOREIGN PATENT DOCUMENTS

| WO | 2009137700 A1 | 11/2009 |
|----|---------------|---------|
| WO | 2018039228 A1 | 3/2018  |

OTHER PUBLICATIONS

Aesculap Spine; Caspar Cervical Retractor System, Product Brochure Apr. 2009 Doc# 510, 16 pages.

Biomet Spine, "Timberline Lateral Fusion System, Surgical Technique Guide", Copyright 2014, 52 pages.

Biomet Spine; AccuVision Minimally Invasive Spinal Exposure System, Surgical Technique Dec. 2009, 28 pages.

Biomet Spine; VuePASS, Surgical Technique Jun. 2007 P/N 216001L. 36 pages.

Depuy; Pipeline Concorde, Surgical Technique Jul. 2007 M102-20-001, 24 pages.

K2M; Tera Nova, Product Brochure 2012 K2-15-7002-01 Rev.3, 2 pages.

Krause et al., U.S. Appl. No. 62/546,780, filed Aug. 17, 2017, titled "Lateral Access Alignment Guide and Rigid Arm".

LANX; Timberline Lateral Fusion System, Surgical Technique LIT8710-0111.03, copyright 2012, Lanx Inc., Broomfield, Co. 42 pages.

Medtronic; Mast Quadrant, Product Brochure 2005 MLITQUDST5, 40 pages.

Milz et al., U.S. Appl. No. 62/560,910, filed Sep. 20, 2017, titled "Spinal Implants".

Milz et al., U.S. Appl. No. 62/319,513, filed Apr. 7, 2016, titled "Expandable Interbody Implant."

NuVasive; Maxcess-XLIF, Surgical Technique 2007 9500138 A.0, 32 pages.

Popejoy et al., U.S. Appl. No. 62/546,796, filed Aug. 17, 2017, titled "Bridges and Lighting for Lateral Access".

Synthes; Oracle Spacer, Technique Guide Dec. 2010 J8158-C, 40 pages.

Wills et al., U.S. Appl. No. 62/103,276, filed Jan. 14, 2015, titled "Spinal Implant With Porous and Solid Surfaces".

Zimmer Spine; Harmony Retractor System, Surgical Technique L1477 Rev. A Aug. 2009, 20 pages.

Zimmer; ARAS Retractor, Surgical Technique L1377 Rev. A 2007, 20 pages.

\* cited by examiner

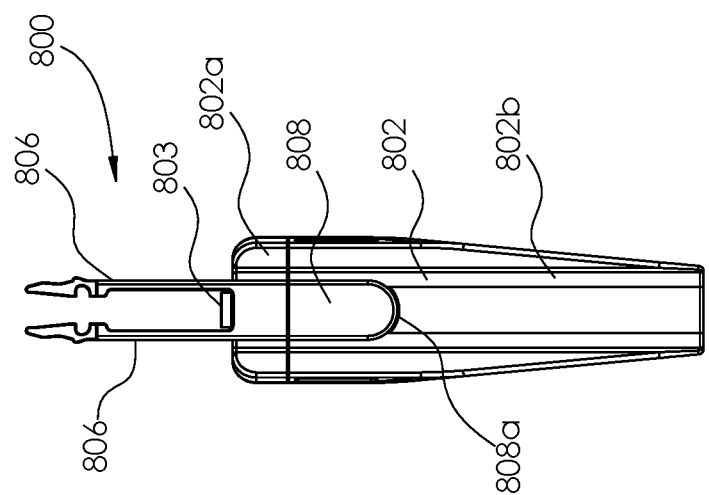
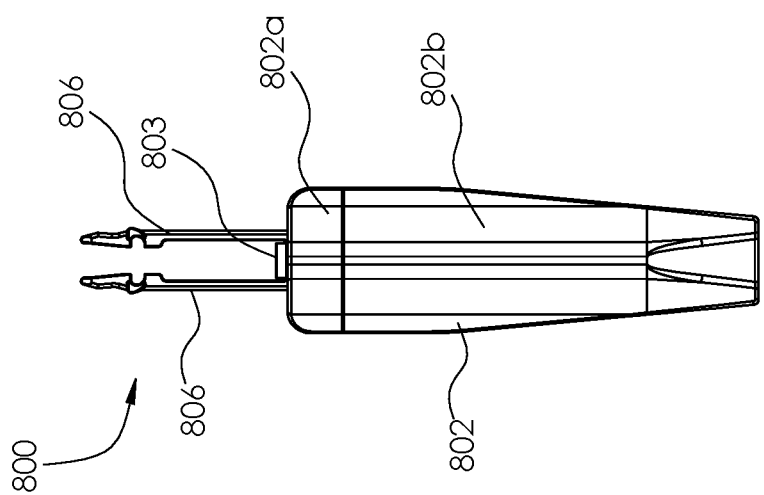
FIG. 17a
FIG. 17b

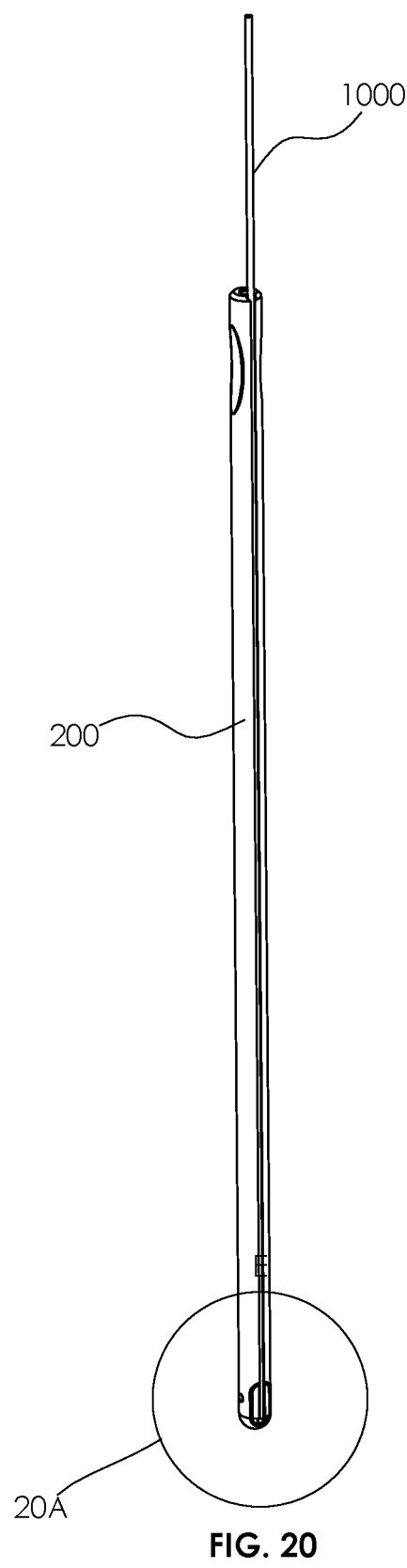
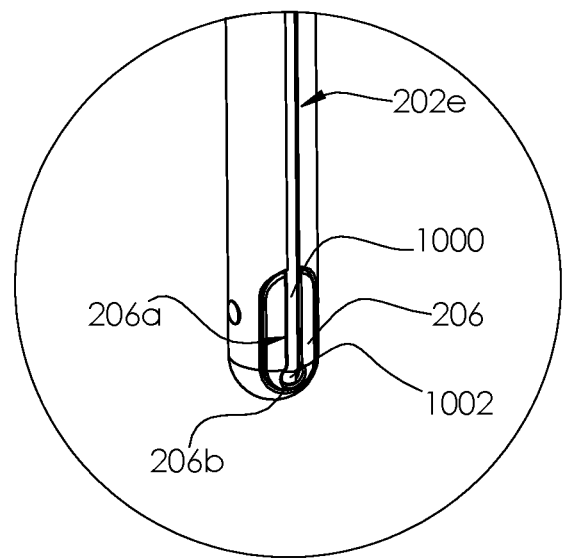
FIG. 20
FIG. 20A

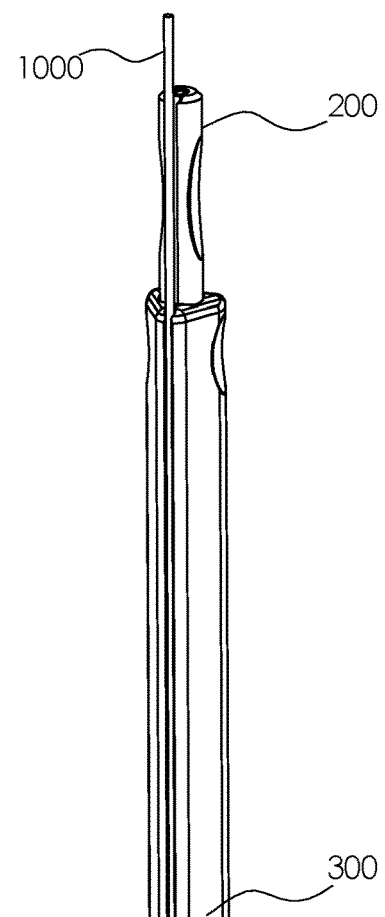
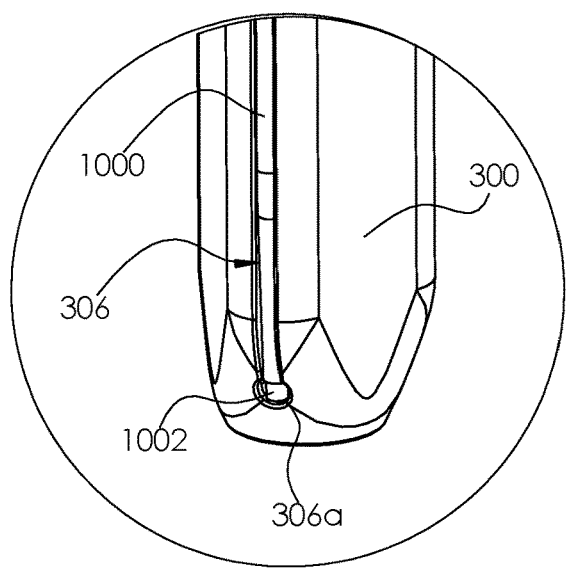
FIG. 22A
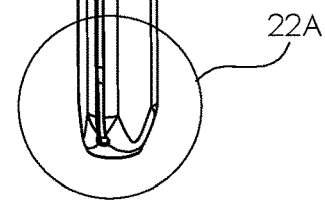
FIG. 22

LATERAL ACCESS SYSTEM AND METHOD OF USE

CROSS-REFERENCE TO RELATED APPLICATIONS

This application claims the benefit of and priority to U.S. Provisional Patent Application No. 62/941,096, filed Nov. 27, 2019, the entire disclosure of which is incorporated by reference herein.

FIELD

The present disclosure relates to devices used in accessing a spinal work location. More particularly, the present disclosure relates to devices and methods for laterally accessing a spinal work location.

BACKGROUND

Disease, the effects of aging, or physical trauma resulting in damage to the spine has been treated in many instances by fixation or stabilization of the affected vertebra. A wide variety of spinal fixation devices have been employed in surgical procedures for correcting spinal injuries and the effects of spinal diseases.

After a partial or complete discectomy, the normally occupied spaced between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. As is typical, the intervertebral spaces are accessed either anteriorly or posteriorly. It would be desirable to access the intervertebral spaces via a lateral approach.

SUMMARY

In accordance with an embodiment of the present disclosure, a surgical retractor includes a body portion and first and second retractor arms operatively coupled to the body portion. The body portion includes a rotatable knob, a first blade holder, and a first blade detachably secured with the first blade holder. The first blade holder is operatively coupled with the rotatable knob such that rotation of the rotatable knob causes axial displacement of the first blade holder. The first blade is configured for axial displacement with the first blade holder and angulation relative to the first blade holder about a first axis. The first and second retractor arms include respective second and third blades detachably secured thereto. The first and second retractor arms are transitionable between an approximated configuration in which the second and third blades are proximate each other, and a spaced apart configuration in which the second and third blades are spaced apart from each other. The second and third blades are configured to angulate about respective second and third axes that are defined by the respective first and second retractor arms.

In an embodiment, at least a portion of the first or second retractor arms may be made of a carbon fiber material.

In another embodiment, at least a portion of the first blade, second blade or third blade may be made of a carbon fiber material.

In yet another embodiment, at least a portion of the first blade, second blade or third blade may be made of metal.

In an embodiment, the first and second retractor arms may be pivotably coupled to respective opposing sides of the body portion.

In another embodiment, the first blade holder may be configured to secure the first blade thereto by a locking screw.

In yet another embodiment, the first blade may be configured for axial displacement independent of the angulation thereof.

In still yet another embodiment, the first blade may be configured to angulate about the first axis orthogonal to a longitudinal axis defined by the body portion.

In an embodiment, the first and second retractor arms may include a ratchet mechanism to maintain respective relative positions of the first and second retractor arms with respect to the body portion.

In another embodiment, the first or second retractor arm may include a handle portion, an arm toeing base, and a blade holder configured to secure the corresponding second or third blade thereto. The blade holder may be coupled to the arm toeing base by a toeing screw that is rotatable to enable the blade holder to rotate relative to the arm toeing base.

In an embodiment, the first, second, and third blades may be configured to define a cavity when proximate each other.

In another embodiment, at least a portion of the arm toeing base may be made of a carbon fiber material.

In yet another embodiment, at least a portion of the blade holder is made of a carbon fiber material.

In another embodiment, the cavity may have a triangular shape.

In yet another embodiment, the first blade is configured to support an intradiscal shim.

In still yet another embodiment, the first blade may be configured to lock a relative position of the intradiscal shim thereto.

In still yet another embodiment, when the first and second retractor arms are in the approximated configuration, the second and third blades may define a gap of about 1 mm.

In accordance with another embodiment of the present disclosure, a method of surgery includes inserting an inner cylindrical dilator through psoas muscle; positioning the inner cylindrical dilator onto a disc; advancing an intradiscal guidewire into the disc through the inner cylindrical dilator; placing an outer triangular dilator over the intradiscal guidewire and the inner cylindrical dilator; transitioning first and second retractor arms of a surgical retractor to an approximated position to place first and second blades coupled to the respective first and second retractor arms proximate each other; placing the first and second blades adjacent the outer triangular dilator; rotating a rotatable knob of the surgical retractor to cause axial displacement of a posterior blade of the surgical retractor towards the first and second blades such that the first and second blades and the posterior blade define a triangular opening around the outer triangular dilator; advancing the first and second blades and the posterior blade along the outer triangular dilator into tissue to engage a spine; and manipulating the first blade, the second blade, or the posterior blade to provide access to the spine.

In an embodiment, manipulating the first blade, the second blade, or the posterior blade may include angulating the first blade, the second blade, or the posterior blade.

In another embodiment, transitioning the first and second retractor arms may include pivoting the first and second retractor arms about respective pivots.

In yet another embodiment, the method may further include determining a blade length of the first and second blades by reading markings on the outer triangular dilator in relation to a skin level.

In still yet another embodiment, the method may further include mounting the first, second, and posterior blades to the surgical retractor.

In still yet another embodiment, the method may further include securing the surgical retractor to an operating table via table mounts.

In still yet another embodiment, the method may further include attaching an intradiscal shim to the posterior blade.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 14b is a rear view of the intradiscal shim of FIG. 14a;

FIG. 15 is a side cross-sectional view of the surgical retractor of FIG. 2, illustrating use with the intradiscal shim of FIG. 14a;

FIG. 17a is a front view of a lengthening shim for use with the surgical retractor of FIG. 1;

FIG. 17b is a rear view of the lengthening shim of FIG. 17a;

FIG. 20 is a perspective view of the inner cylindrical dilator of FIG. 19, illustrating advancement of the stimulation probe;

FIG. 20A is an enlarged view of the indicated area of detail of FIG. 20;

FIG. 22 is a perspective view of the dilator assembly of FIG. 11, illustrating advancement of the stimulation probe;

FIG. 22A is an enlarged view of the indicated area of detail of FIG. 22;

DETAILED DESCRIPTION

Figure 1:
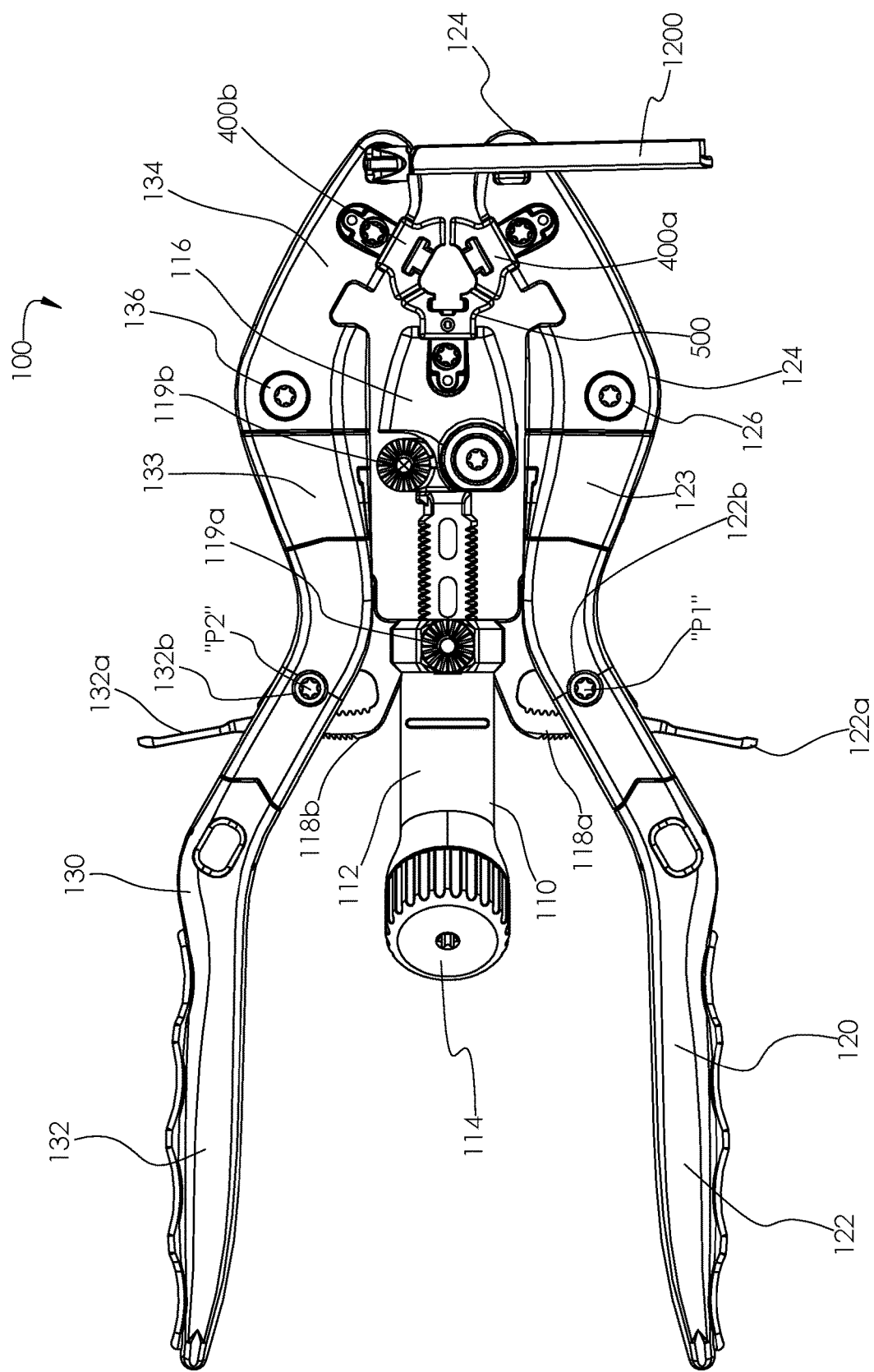
FIG. 1 is a top view of a surgical retractor in accordance with an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments.

Figure 2:
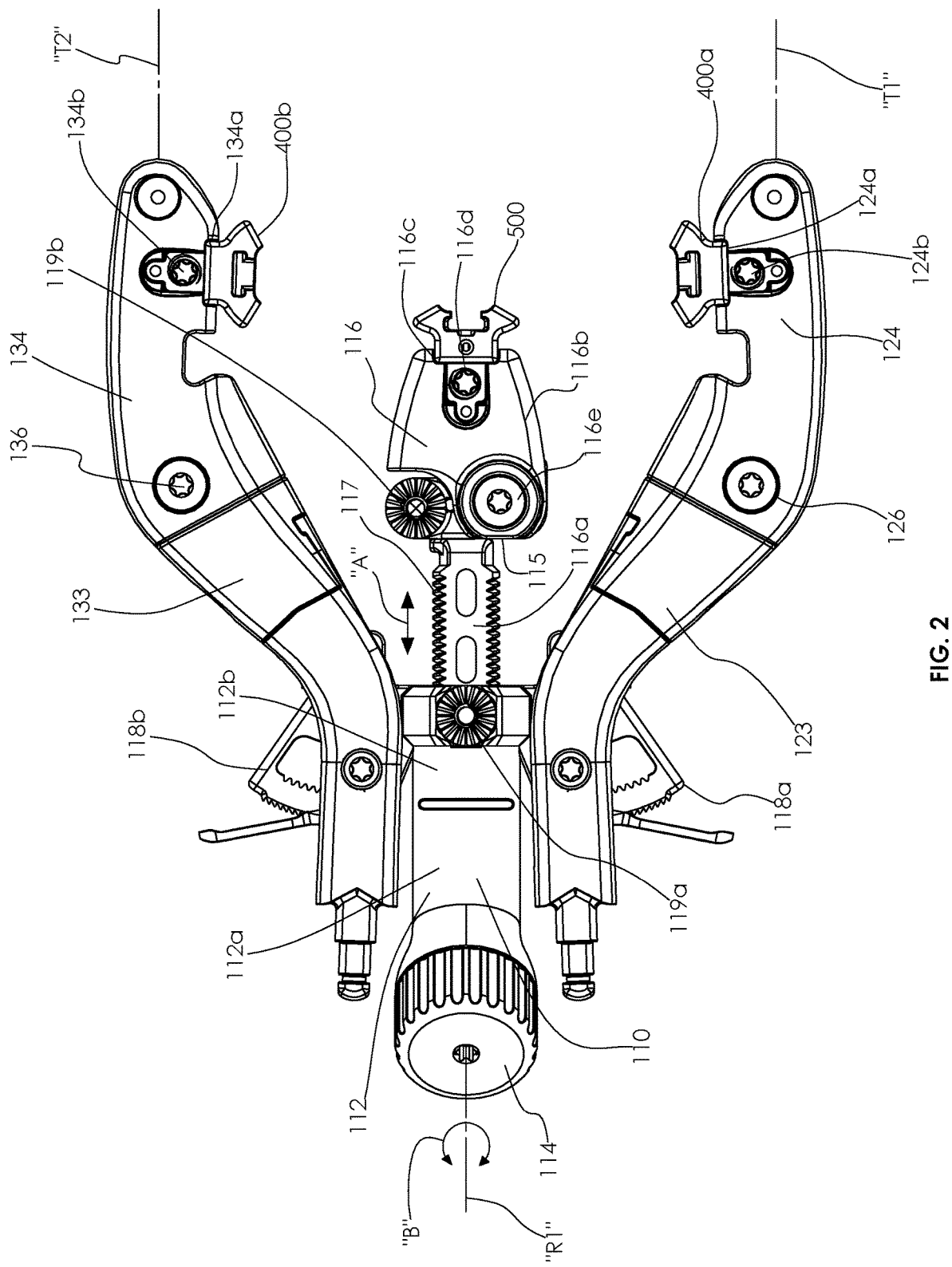
FIG. 2 is a partial top view of the surgical retractor of FIG. 1, illustrating the surgical retractor in a spaced apart configuration.
Figure 3:
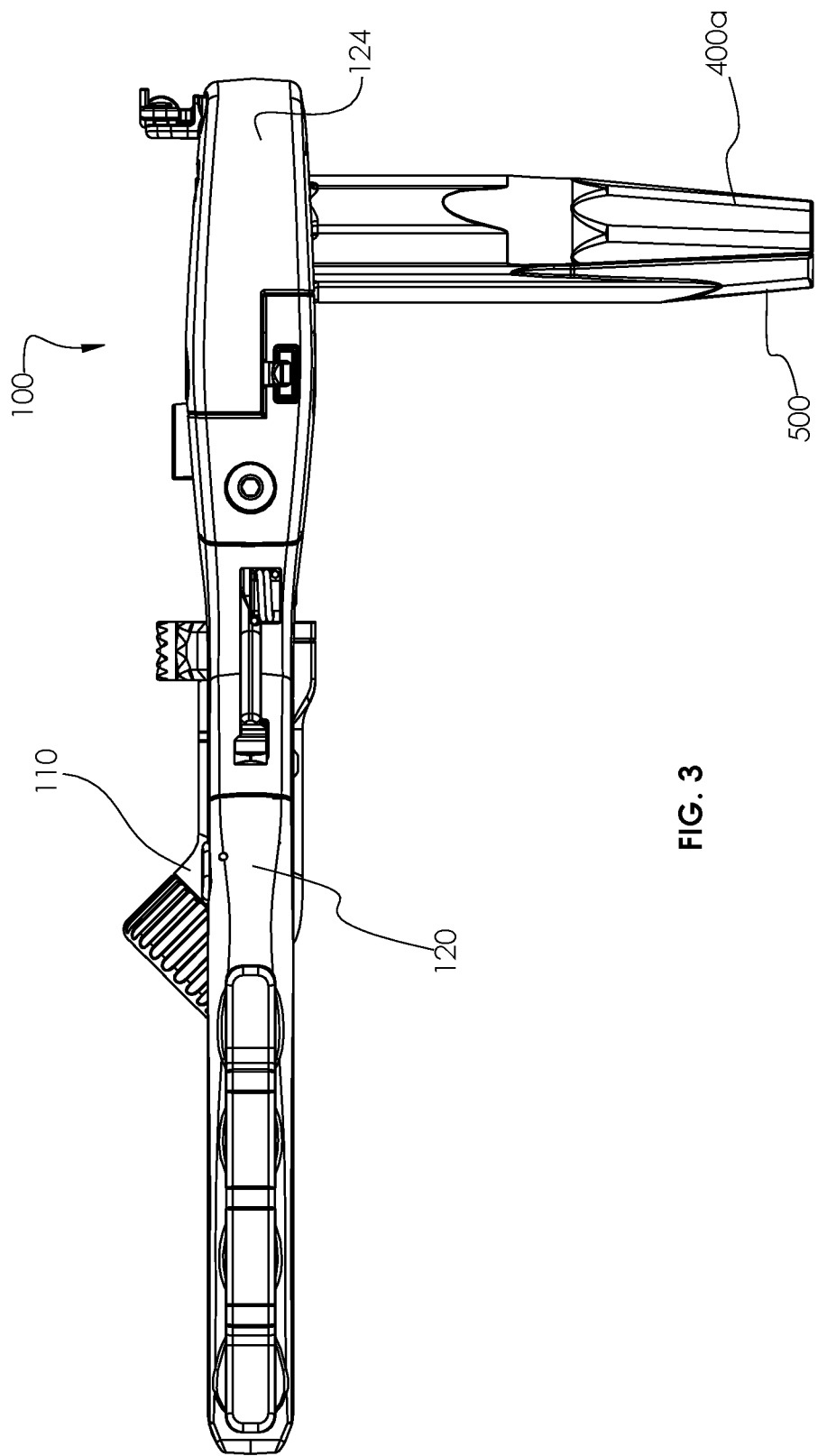
FIG. 3 is a side view of the surgical retractor of FIG. 1.

With initial reference to FIGS. 1 and 2, a surgical retractor in accordance with an embodiment of the present disclosure is generally shown as a surgical retractor 100. The surgical retractor 100 may be utilized in accessing, e.g., lumbar vertebrae, using a trans-psoas approach. It is contemplated that the surgical retractor 100 may be utilized in, e.g., discectomy, laminectomy, transforaminal or posterior lumbar interbody fusion (TLIF/PLIF), or posterior fixation (e.g., pedicle screw system). The surgical retractor 100 enables the surgeon to perform, e.g., an open procedure, in minimal space with reduced tissue damage. The surgical retractor 100 used in such procedures may reduce blood loss, improve recovery time, and/or reduce scarring. The surgical retractor 100 may be used as part of a lateral access surgical system including a dilator assembly 301 (FIG. 11) including an inner cylindrical dilator 200 (FIG. 12) and an outer triangular dilator 300 (FIG. 13), an intradiscal shim 600 (FIG. 14a), a widening shim 700 (FIG. 16a), a lengthening shim 800 (FIG. 18), an intradiscal guidewire 900 (FIG. 11a), and a stimulation probe 1000 (FIG. 19), as will be described below.

With reference to FIG. 1, the surgical retractor 100 includes a tube assembly 110 and first and second retractor arms 120, 130 operatively coupled to respective opposing sides of the tube assembly 110. In particular, the first and second retractor arms 120, 130 are pivotably coupled to the tube assembly 110 about respective pivots "P1", "P2" such that distal ends of the respective first and second retractor arms 120, 130 are transitionable between an approximated position (FIG. 1) and a spaced part position (FIG. 2).

With particular reference to FIG. 2, the tube assembly 110 includes a tube body 112 supporting a rotatable knob 114 on a proximal end 112a thereof and a posterior blade holder assembly 116 supported on distal end 112b thereof. The posterior blade holder assembly 116 includes a shaft arm assembly 116a, a posterior blade holder 116b supported on a distal end of the shaft arm assembly 116a, and a posterior blade 500 mounted on the posterior blade holder 116b. The shaft arm assembly 116a is operatively coupled to the rotatable knob 114 such that rotation of the rotatable knob 114 in the direction of arrows "B" (about an axis "R1") causes axial displacement of the posterior blade holder 116b, and thus, the posterior blade 500 in the direction of arrows "A". In an embodiment, the shaft arm assembly 116a may include threads 117 that threadably engage the tube body 112. The threads 117 are disposed on lateral sides of the shaft arm assembly 116a to optimize load distribution. However, it is contemplated that the threads 117 may be disposed on top and bottom surfaces of the shaft arm assembly 116a. Under such a configuration, the clinician may position the posterior blade 500 at a desired position, e.g., away from the tube body 112.

With continued reference to FIG. 2, the posterior blade holder 116b includes a posterior blade seat 116c configured to, e.g., detachably, secure the posterior blade 500 thereto. For example, the posterior blade 500 may be detachably secured to the posterior blade seat 116c by a locking screw 116d. Alternatively, the posterior blade 500 may be detachably secured to the posterior blade holder 116b by, e.g., snap fit or friction fit.

In an embodiment, the posterior blade 500 may be integrally formed with the posterior blade holder 116b as a single construct. Under such a configuration, the posterior blade holder assembly 116 may be detachable from the tube body 112 or the shaft arm assembly 116a. The posterior blade holder 116b further includes a posterior toeing screw 116e. The posterior toeing screw 116e is rotatable to enable the posterior blade 500 to toe (i.e., angulate) relative to the shaft arm assembly 116a. For example, the posterior blade 500 may be rotated about an axis orthogonal to the length of the posterior blade 500 to angulate opposing ends of the posterior blade 500 in opposite directions in a range from about 0 degrees to about 30 degrees. The posterior toeing screw 116e defines a cavity 119 having, e.g., a hex key feature, for non-slip engagement with a driving instrument to drive the posterior toeing screw 116e to cause toeing of the posterior blade 500. However, it is further contemplated that the cavity 119 may have any suitable configuration (e.g., slotted, hexagonal, square, etc.) for engagement with a complementary driving instrument. Under such a configuration, the posterior blade 500 is configured for selective axial displacement (towards and away from the tube body 112) and toeing (rotation about an axis orthogonal to the length of the posterior blade 500) by the clinician.

Figure 6:
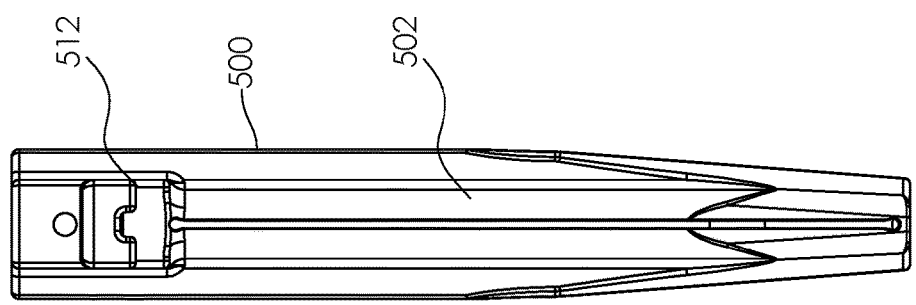
FIG. 6 is a rear view of the posterior blade of FIG. 5.
Figure 5:
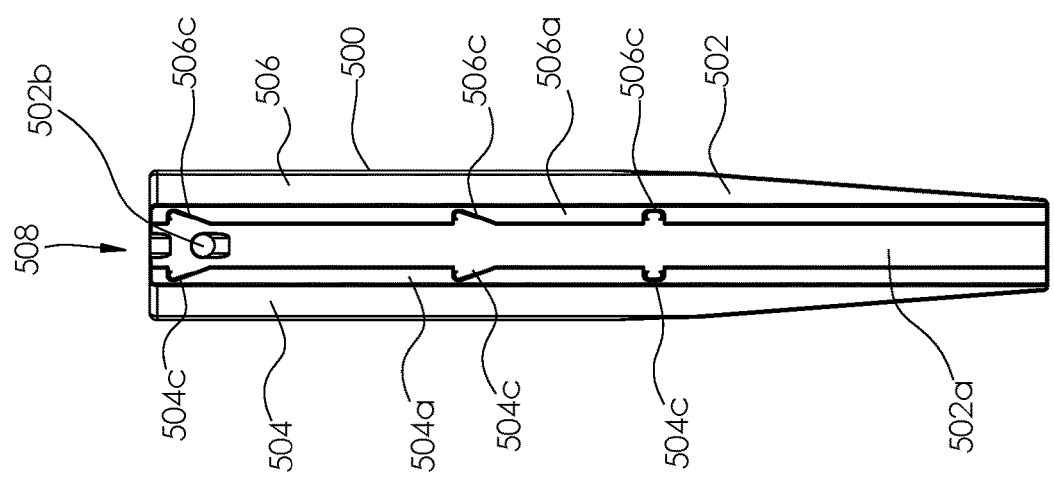
FIG. 5 is a front view of a posterior blade of the surgical retractor of FIG. 1.
Figure 7:
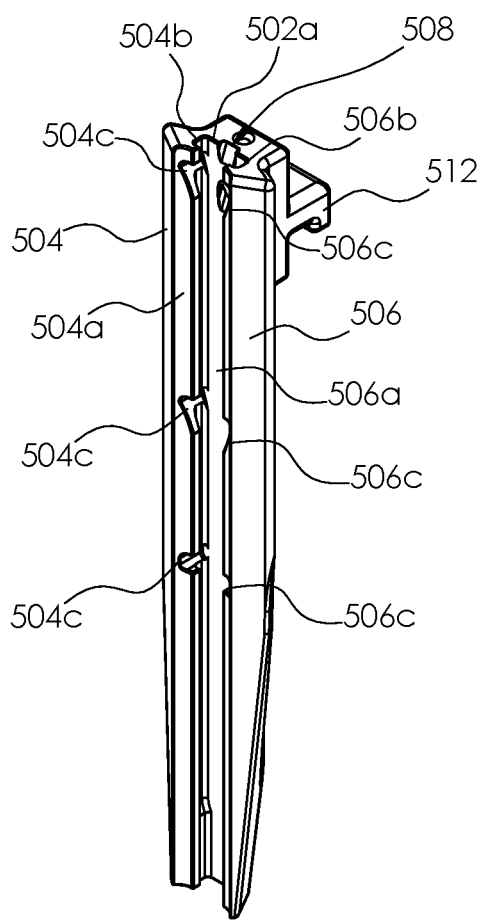
FIG. 7 is a perspective view of the posterior blade of FIG. 5.
Figure 9:
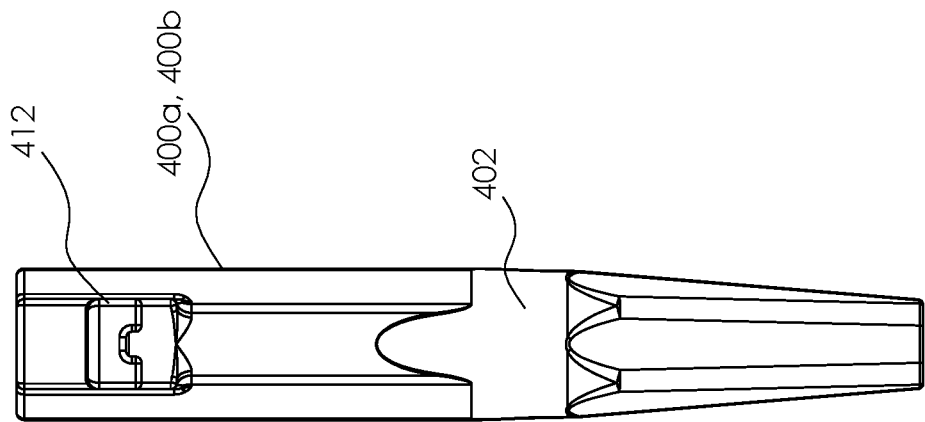
FIG. 9 is a rear view of the first or second blade of FIG. 8.
Figure 11:
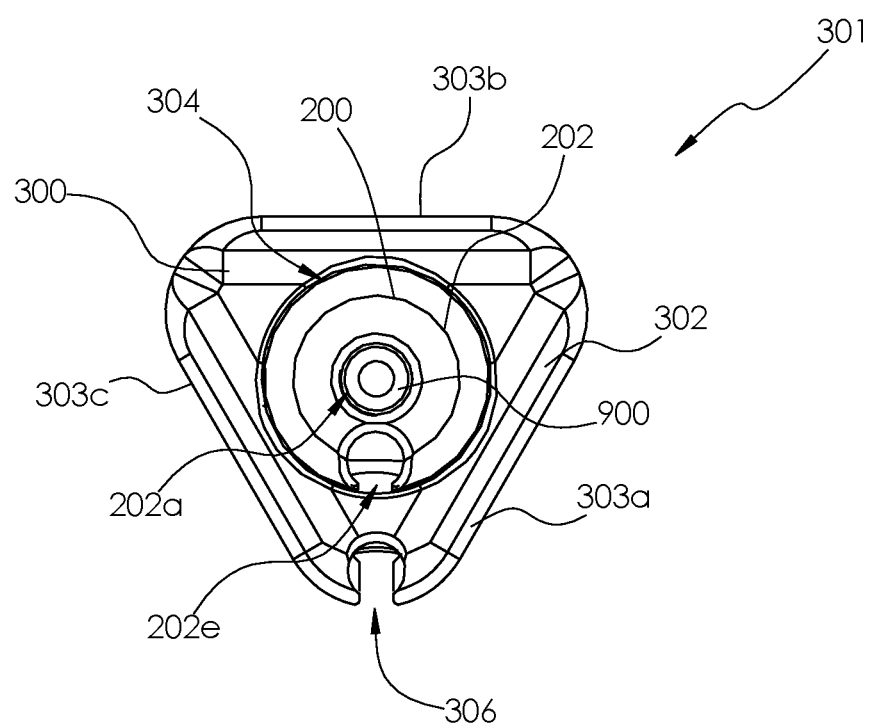
FIG. 11 is a cross-sectional view of a dilator assembly for use with the surgical retractor of FIG. 1.
Figure 11A:
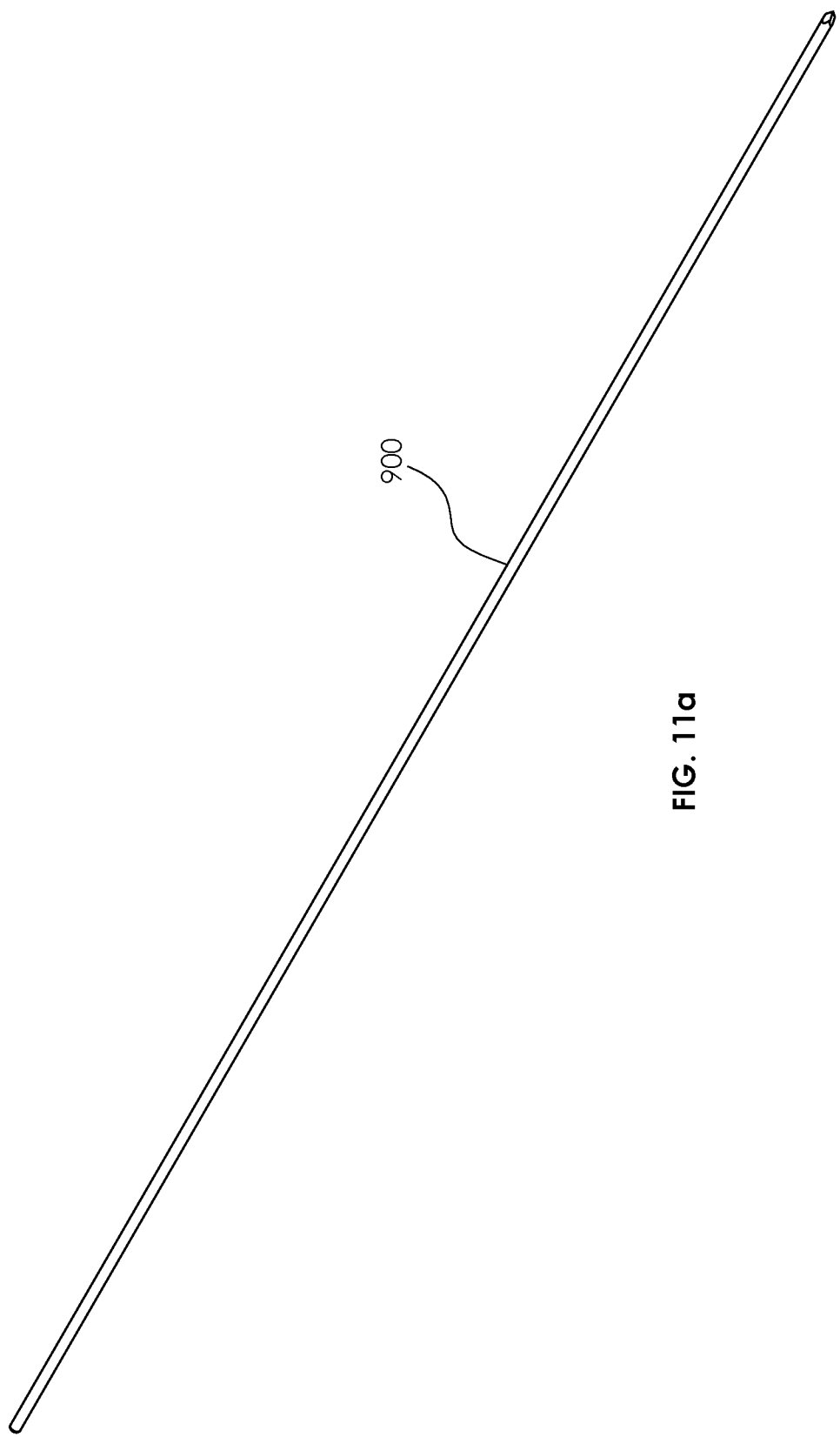
FIG. 11a is a perspective view of an intradiscal guidewire for use with the surgical retractor of FIG. 1.
Figure 13:
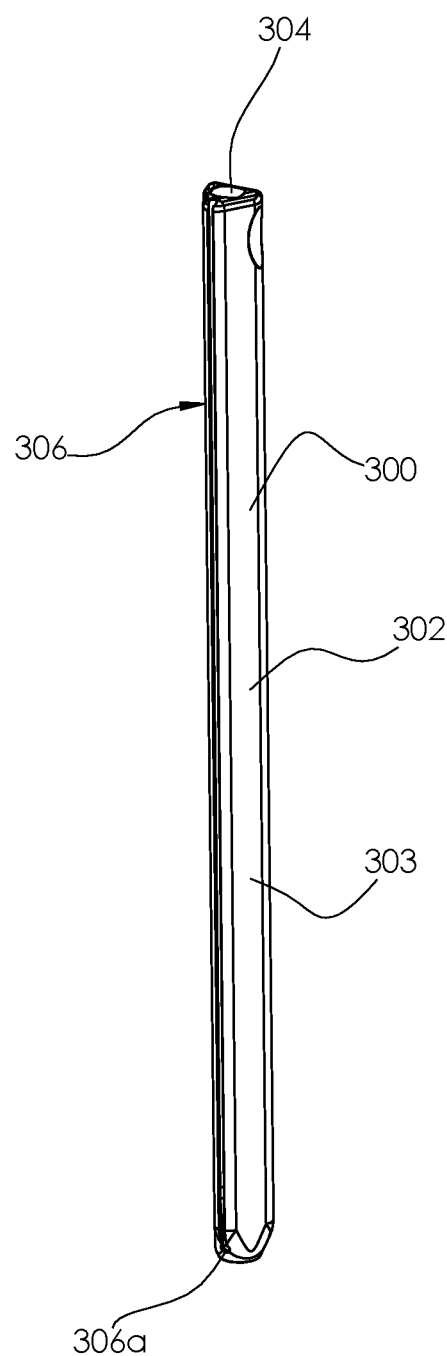
FIG. 13 is a perspective view of an outer triangular dilator of the dilator assembly of FIG. 11.
Figure 13A:
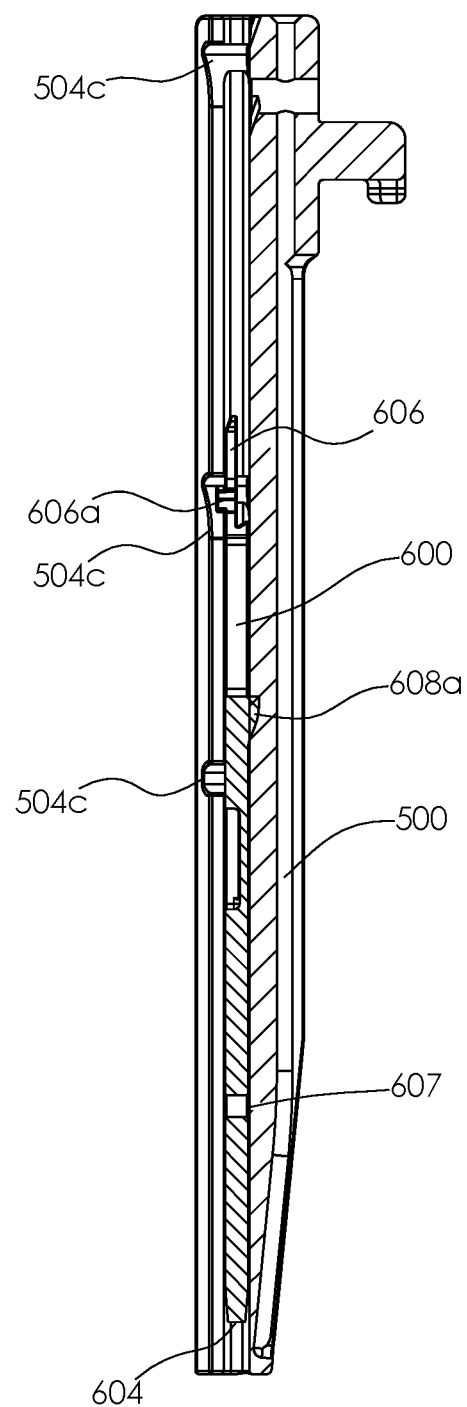
FIGS. 13a and 13b are cross-sectional views of the posterior blade of FIG. 5, illustrating use with an intradiscal shim.
Figure 14B:
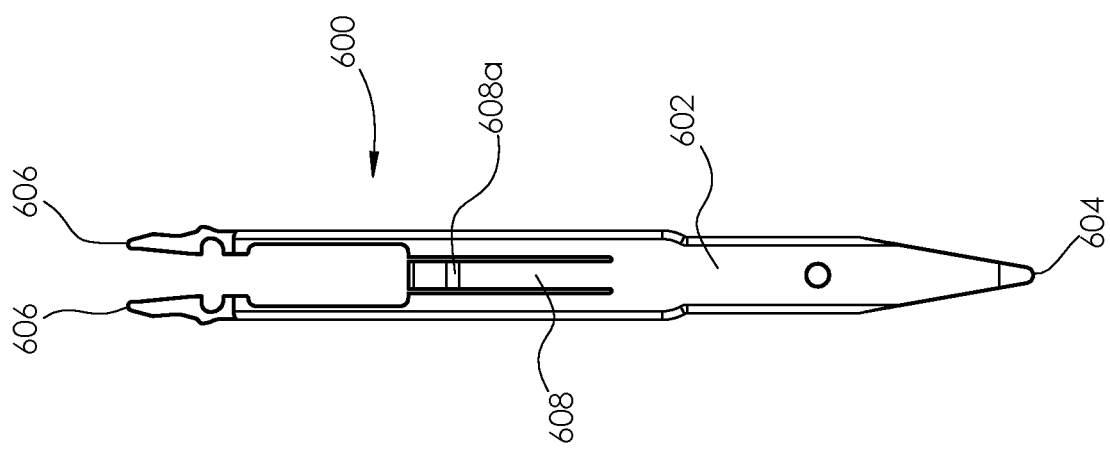
Figure 14A:
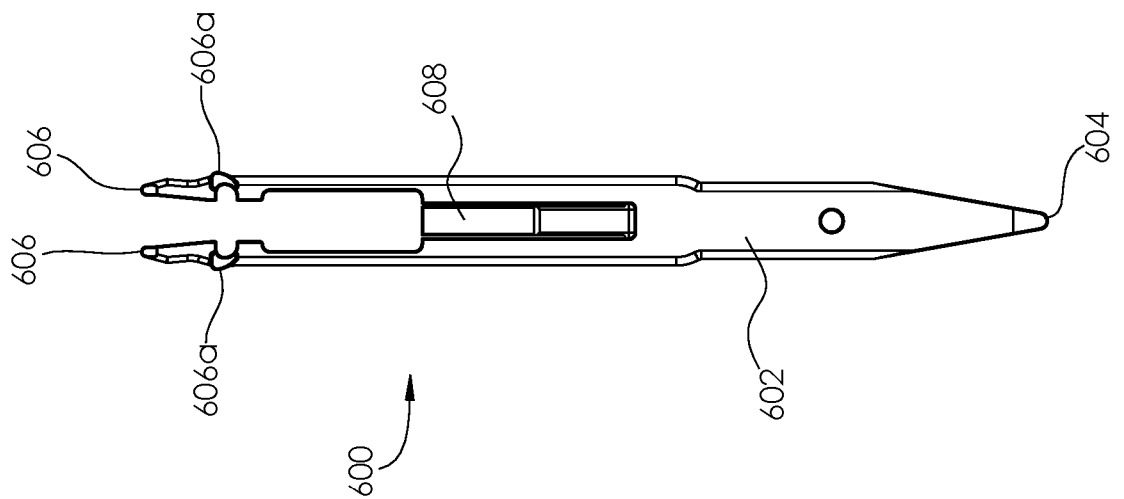
FIG. 14a is a front view of the intradiscal shim of FIGS. 13a and 13b.

With reference to FIGS. 5-7, the posterior blade 500 has a blade body 502 including first and second rails 504, 506 that project from a planar inner surface 502a of the blade body 502 to engagement surfaces 504a, 506a of the respective first and second rails 504, 506. The first and second rails 504, 506 taper inwardly toward one another and define cutouts 504b, 506b so that the first and second rails 504, 506 overhang a planar inner surface 502a to define an open longitudinal receiving trough 508 that is c-shaped for retaining an intradiscal shim 600 (FIGS. 14a and 14b). The engagement surfaces 504a, 506a are configured to complement an outer surface 303 of an outer triangular dilator 300 (FIGS. 11 and 13). The planar inner surface 502a defines a recess 502b in a proximal end portion thereof. The first and second rails 504, 506 further include cutouts 504c, 506c, respectively, that extend into open longitudinal receiving trough 508 for limiting insertion depth or retraction of the intradiscal shim 600 relative to the posterior blade 500. The cutouts 504c, 506c are also configured to lock the intradiscal shim 600 at a fixed depth. The blade body 502 also includes a mounting hook 512 supported on a proximal end thereof for securing the blade body 502 to the posterior blade seat 116c (FIG. 2) of the posterior blade holder 116b of retractor 100.

With reference back to FIGS. 1-4, the tube assembly 110 further includes mounting wings 118a, 118b that extend from opposing sides of the tube assembly 110. The first and second retractor arms 120, 130 are pivotably coupled to the tube assembly 110 about the first and second pivots "P1" and "P2." The first retractor arm 120 includes a first handle portion 122, a first blade holder 124, and a first arm toeing base 123 configured to support the first blade holder 124 on the first retractor arm 120. The first blade holder 124 is coupled to the first retractor arm 120 by a first toeing screw 126 that is rotatable to enable first blade holder 124 to toe relative to first arm toeing base 123 about toeing axis "T1" defined through the first retractor arm 120. The first retractor arm 120 further supports a first locking pawl 122a defining a ratchet mechanism with the mounting wing 118a, and the first drive pin 122b that secures the first retractor arm 120 to the mounting wing 118a of the tube assembly 110. The first drive pin 122b defines a first pivot "P1" about which the first drive pin 122b rotates to pivot the first retractor arm 120 relative to the tube assembly 110 and the second retractor arm 130. The first blade holder 124 further includes a first blade seat 124a that supports a first retractor blade 400a and a first locking screw 124b to secure the first retractor blade 400a thereto such that the first retractor blade 400a may angulate with respect to the first arm toeing base 123 when the first toeing screw 126 is rotated.

Figure 4:
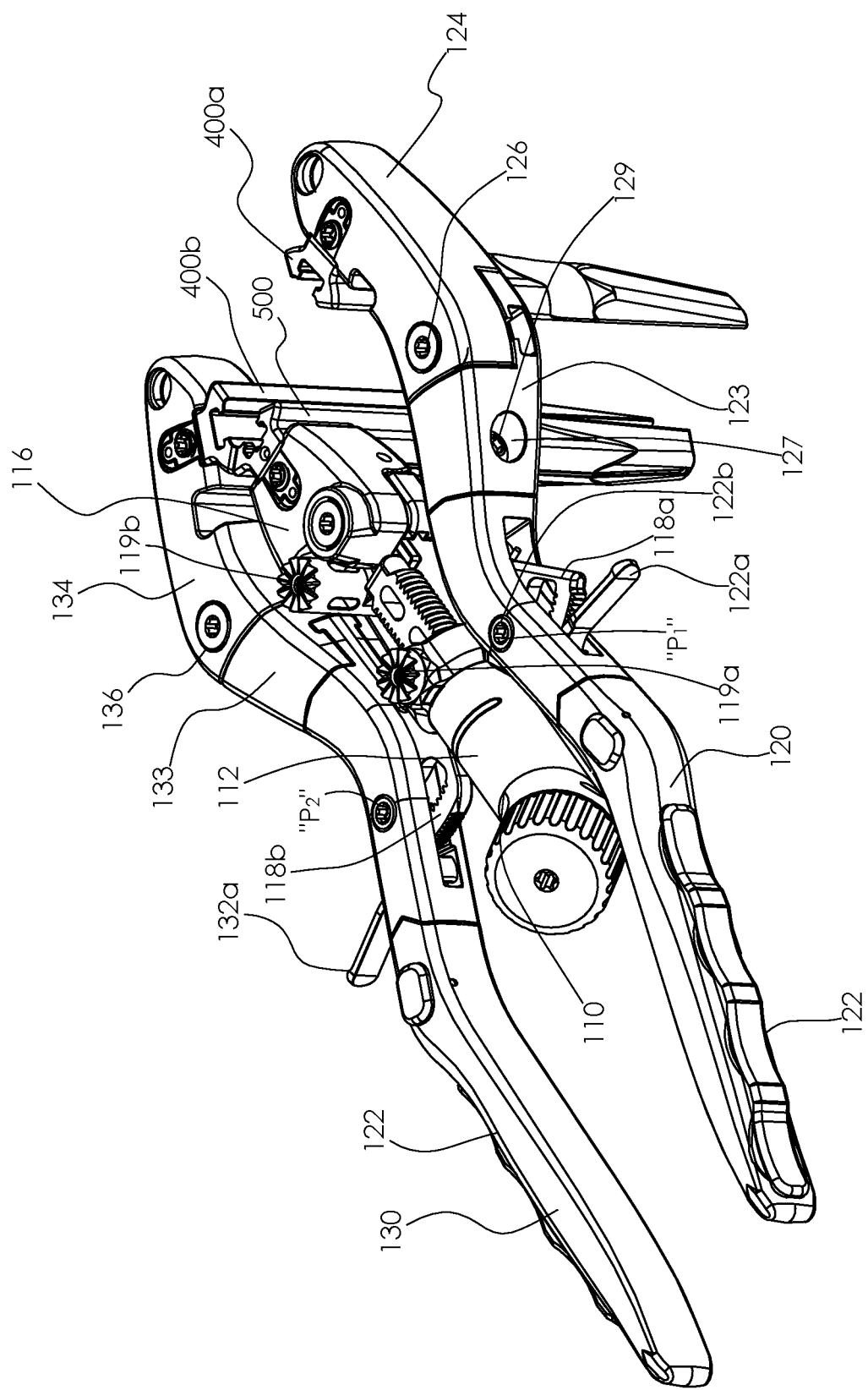
FIG. 4. is a perspective view of the surgical retractor of FIG. 1 in the spaced part configuration.
Figure 4A:
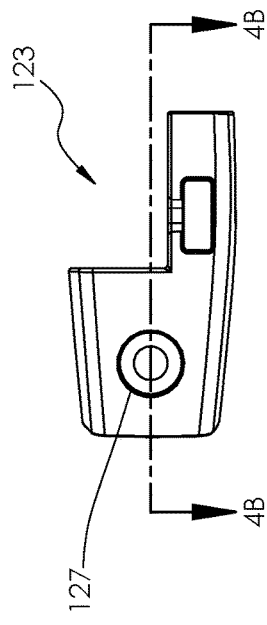
FIG. 4A is a side view of the first toeing base of the surgical retractor of FIG. 1.
Figure 4B:
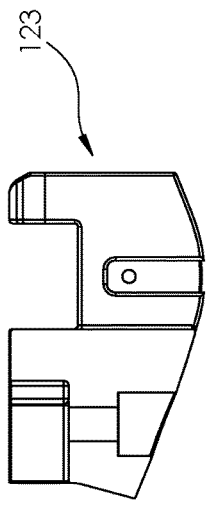
FIG. 4B is a cross-sectional view of the first toeing base of FIG. 4A cut along section line 4B-4B of FIG. 4A.
Figure 4D:
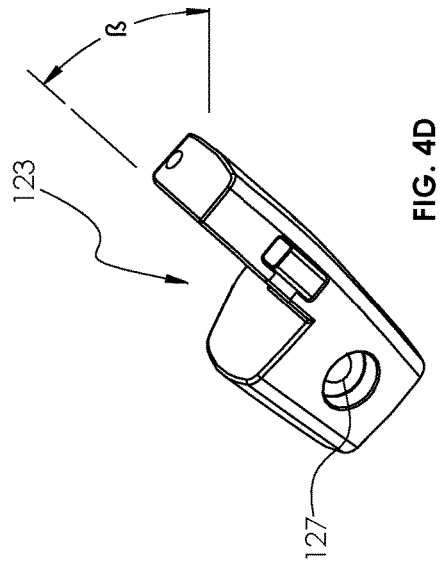
FIGS. 4C and 4D are perspective views of the first toeing base of FIG. 4A, illustrating direction of layers of carbon fiber.
Figure 4C:
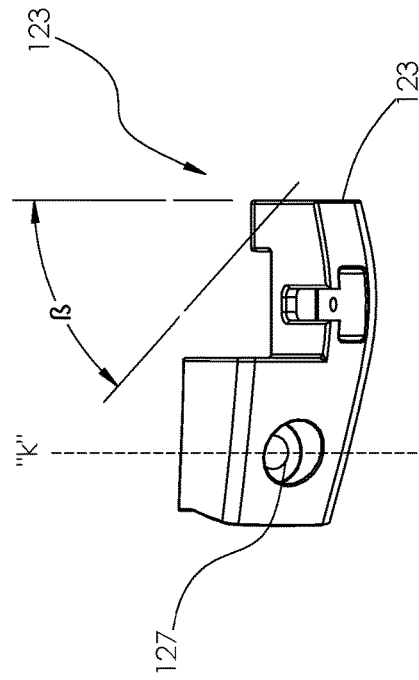

With continued reference to FIGS. 1-4, the second retractor arm 130, which mirrors first retractor arm 120, includes a second handle portion 132, a second blade holder 134, and a second arm toeing base 133 configured to support the second blade holder 134 on the second retractor arm 130. The second retractor arm 130 supports a second locking pawl 132a defining a ratchet mechanism with the mounting wing 118b, and a second drive pin 132b that secures the second retractor arm 132 to the mounting wing 118b of tube assembly 110. The second drive pin 132b defines a second pivot "P2" about which the second drive pin 132b rotates to pivot the second retractor arm 130 relative to the tube assembly 110 and the first retractor arm 120. The second blade holder 134 further includes a second blade seat 134a that supports a second retractor blade 400b and a second locking screw 134b to secure the second retractor blade 400b thereto so that the second retractor blade 400b can angulate with respect to the second arm toeing base 133 when the second toeing screw 136 is rotated. With particular reference to FIG. 4, in an embodiment, the tube assembly 110 may further include a first table mount 119a coupled to tube body 112 and a second table mount 119b coupled to posterior blade holder 116b to mount the surgical retractor 100 to a table.

Figure 25:
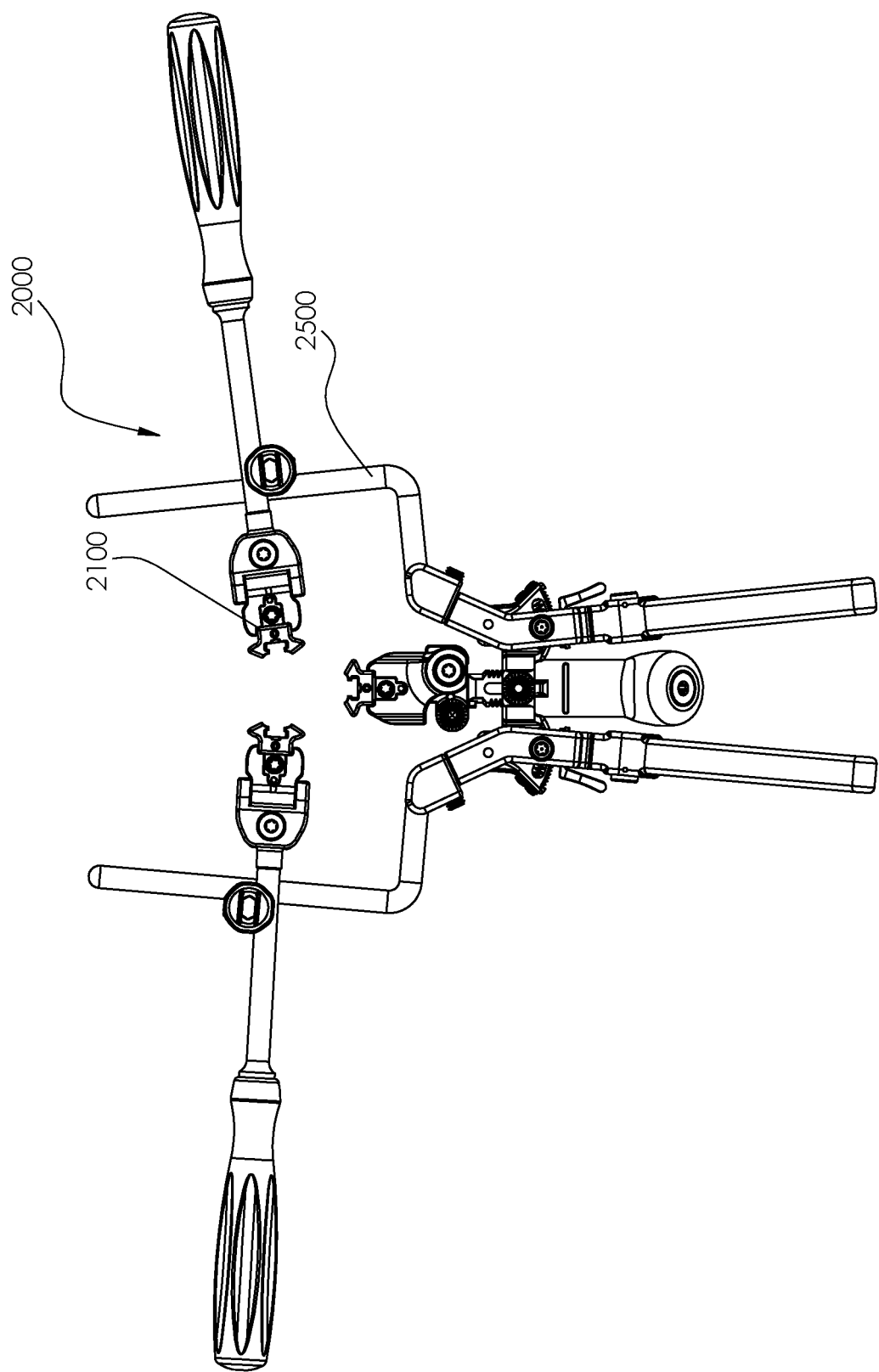
FIG. 25 is a top plan view of the surgical retractor of FIG. 1 with manual blade assemblies.
Figure 26:
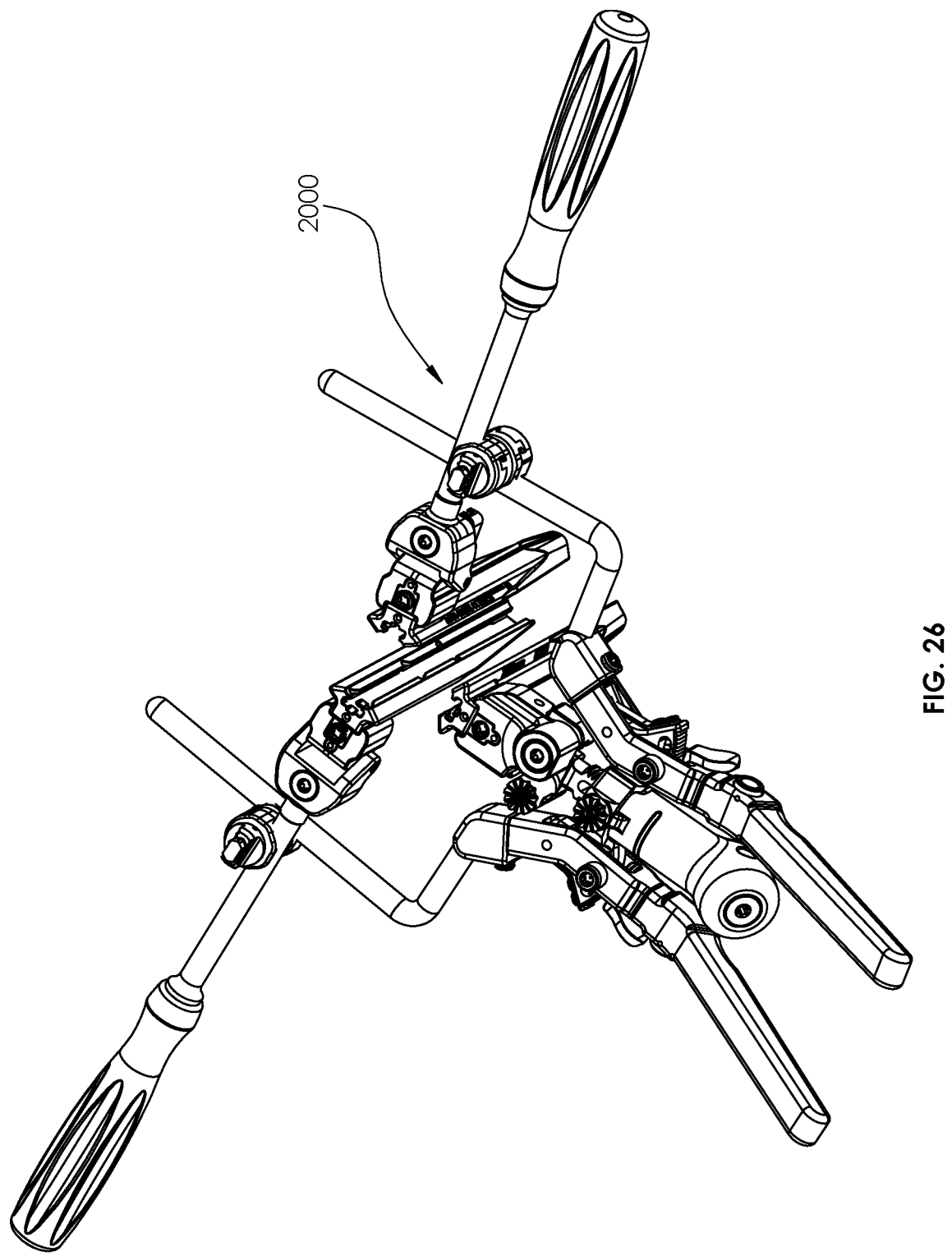
FIG. 26 is a perspective view of the surgical retractor with manual blade assemblies of FIG. 25.
Figure 27:
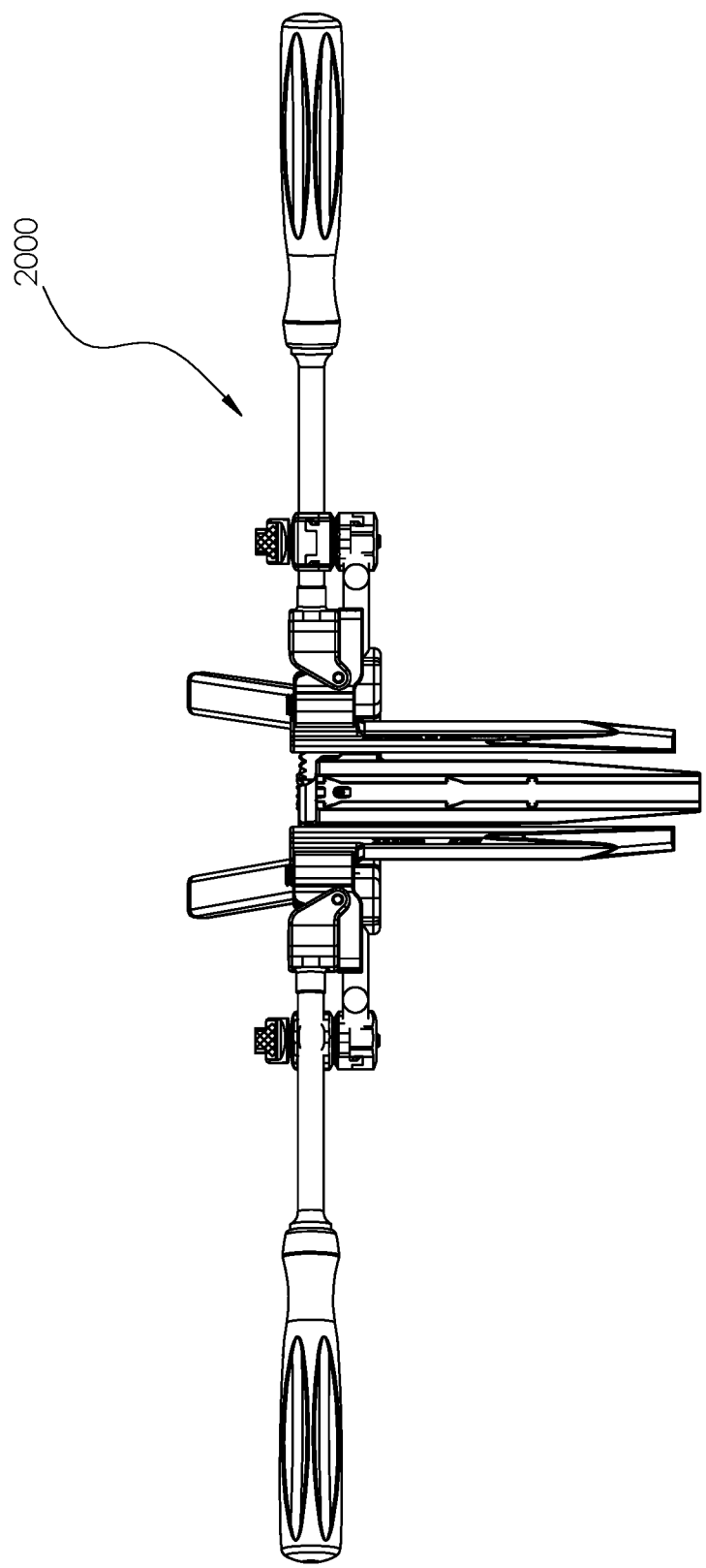
FIG. 27 is a front view of the surgical retractor and manual blade assembly of FIG. 25.

It is contemplated that the first and second arm toeing bases 123, 133 may be formed of a carbon fiber material, such as carbon fiber reinforced or filled polyetheretherketone (PEEK), to enhance structural integrity, reduce weight and improve visualization under imaging. In the interest of brevity, only the first arm toeing base 123 is illustrated in FIGS. 4A-4D, however, the first and second arm toeing bases 123, 133 are mirror images of each other, and thus, the features described herein with respect to the first arm toeing base 123 may be applied to the second arm toeing base 133. In particular, the direction of layers of fiber incorporated into the base may define an angle $\beta$ in the range of about 40 degrees and about 60 degrees, and preferably about 50 degrees, with respect to a leading edge 123 of the first arm toeing base 123 in order to optimize the strength of the part relative to the directional forces experienced during use. Stated differently, the direction of layers of fiber may define the angle $\beta$ with respect to an axis extending across the bore 127 configured to receive a screw 129 (FIG. 4) to secure the first arm toeing base 123 and/or the first blade holder 124 to the first retractor arm 120. The use of the screw 129 facilitates interchangeability of the first arm toeing base 123 and the first blade holder 124 with the manual blade assembly 2000 (FIGS. 25-27) including manual blades 2100 manually movable on a retractor elbow rod 2500. As shown, the manual blade assembly may include rod-style arms attachable to and extending from the handle assembly. Blade assemblies may be attached to the rod-style arms at various locations, such as by a herth-style clamp.

Figure 4E:
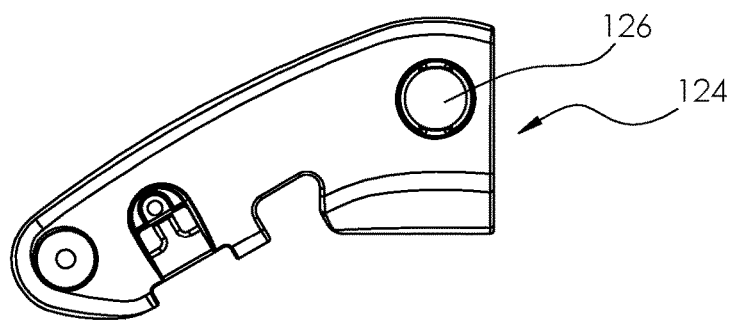
FIG. 4E is a top view of a first blade holder of the surgical retractor of FIG. 1.
Figure 4F:
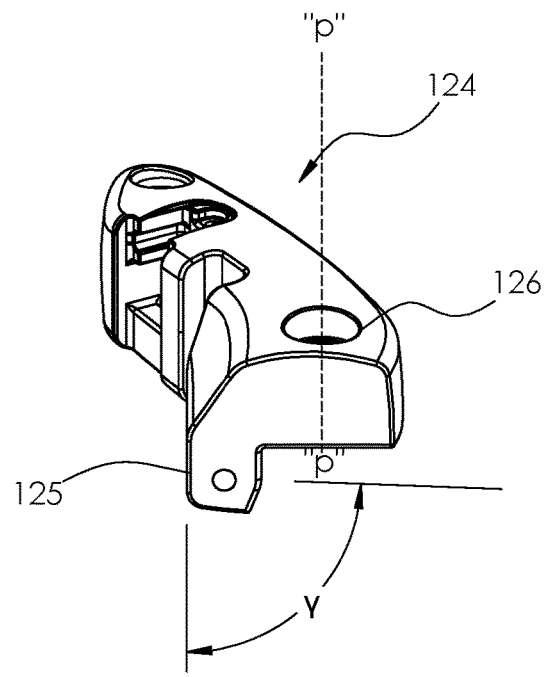
FIG. 4F is a perspective view of the first blade holder of FIG. 4E, illustrating direction of layers of carbon fiber.

With reference to FIGS. 4E and 4F, it is further contemplated that the first and second blade holders 124, 134 also may be formed of a carbon fiber material to enhance structural integrity, reduce weight and improve visualization under imaging. In the interest of brevity, only the first blade holder 124 is shown, however, the first and second blade holders 124, 134 are mirror images of each other, and thus, the features described herein with respect to the first blade holder 124 may be applied to the second blade holder 134. In particular, the direction of layers of fiber may define an angle $\gamma$ in the range of about 80 degrees and about 100 degrees, and preferably about 70 degrees, with respect to a trailing edge 125 of the first blade holder 124 in order to optimize the strength of the part relative to the directional forces experienced during use. The trailing edge 125 may be substantially parallel to an axis "P-P" defined by the bore 126 such that the direction of layers of fiber may define the angle $\gamma$ with respect to axis "P-P". Under such a configuration, the first retractor arm 120 may be partially formed of a carbon fiber material. For example, the first blade holder 124 and the first toeing base 123 may be formed of a carbon fiber material and the rest of the first retractor arm 120 may be formed of stainless steel or aluminum or any other biocompatible material. The use of carbon fiber material for all or part of the toeing bases 123, 133 and/or blade holders 124, 134 enhances visualization of the operative site, including the location and orientation of the retractor relative to the anatomy such as the vertebral bodies and end plates under x-ray or fluoroscopic imaging. This is particularly helpful during placement of the retractor.

Figure 4G:
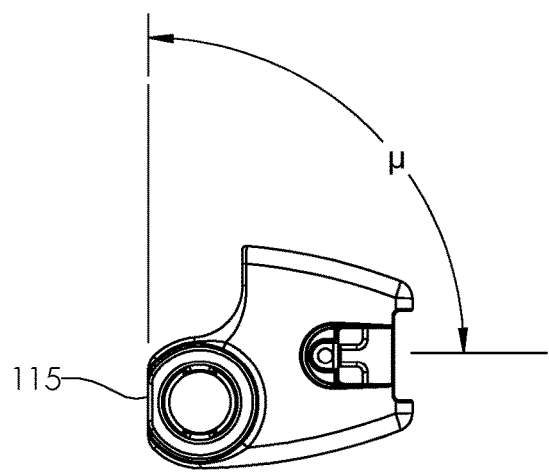
FIG. 4G is a top view of a posterior blade holder assembly of the surgical retractor of FIG. 1.

With reference to FIG. 4G, it is also contemplated that the posterior blade holder assembly 116 (also shown in FIG. 2) may be formed of a carbon fiber material to enhance structural integrity, reduce weight and improve visualization under imaging. In particular, the direction of layers of fiber may define an angle $\mu$ in the range of about 80 degrees and about 100 degrees with respect to a trailing edge 115 of the posterior blade holder assembly 116.

Figure 18:
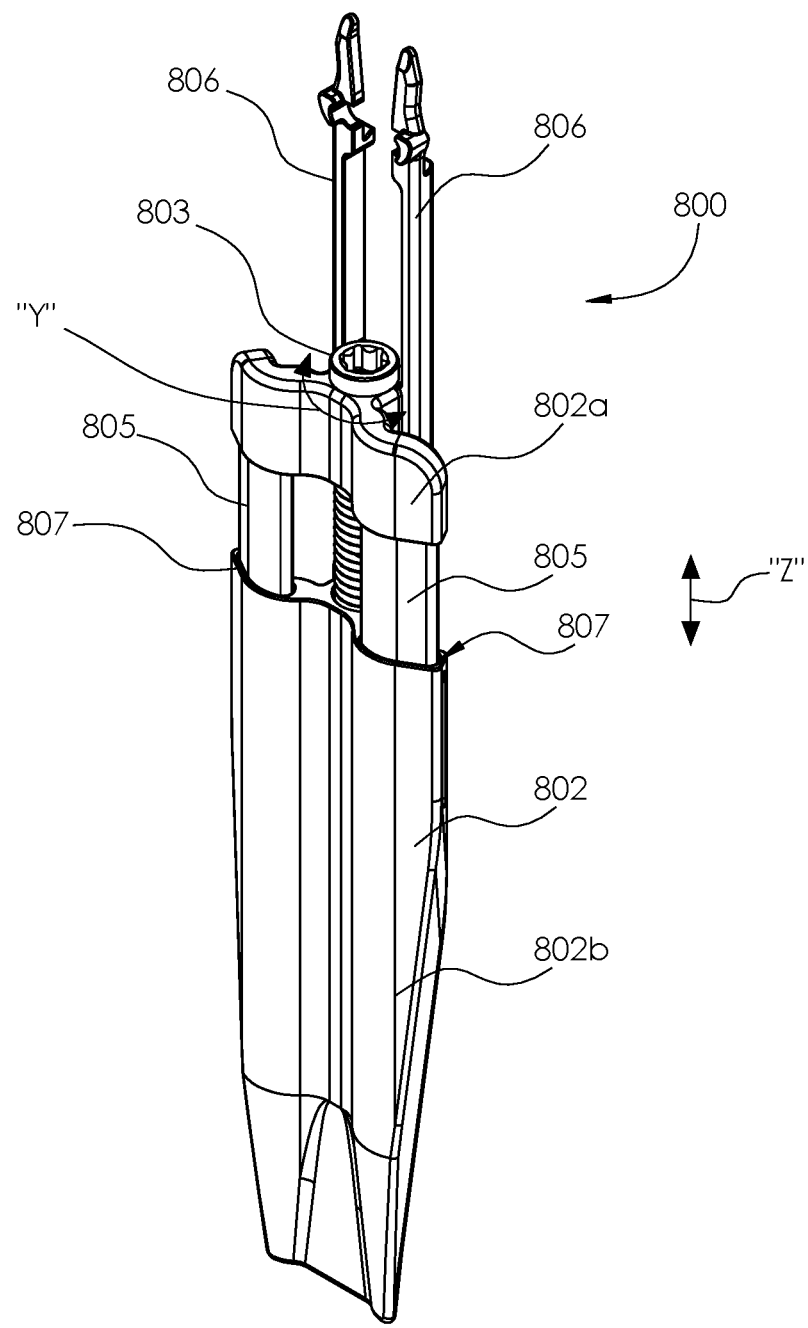
FIG. 18 is a perspective view of the lengthening shim of FIG. 17a in an extended configuration.
Figures 19, 19A:
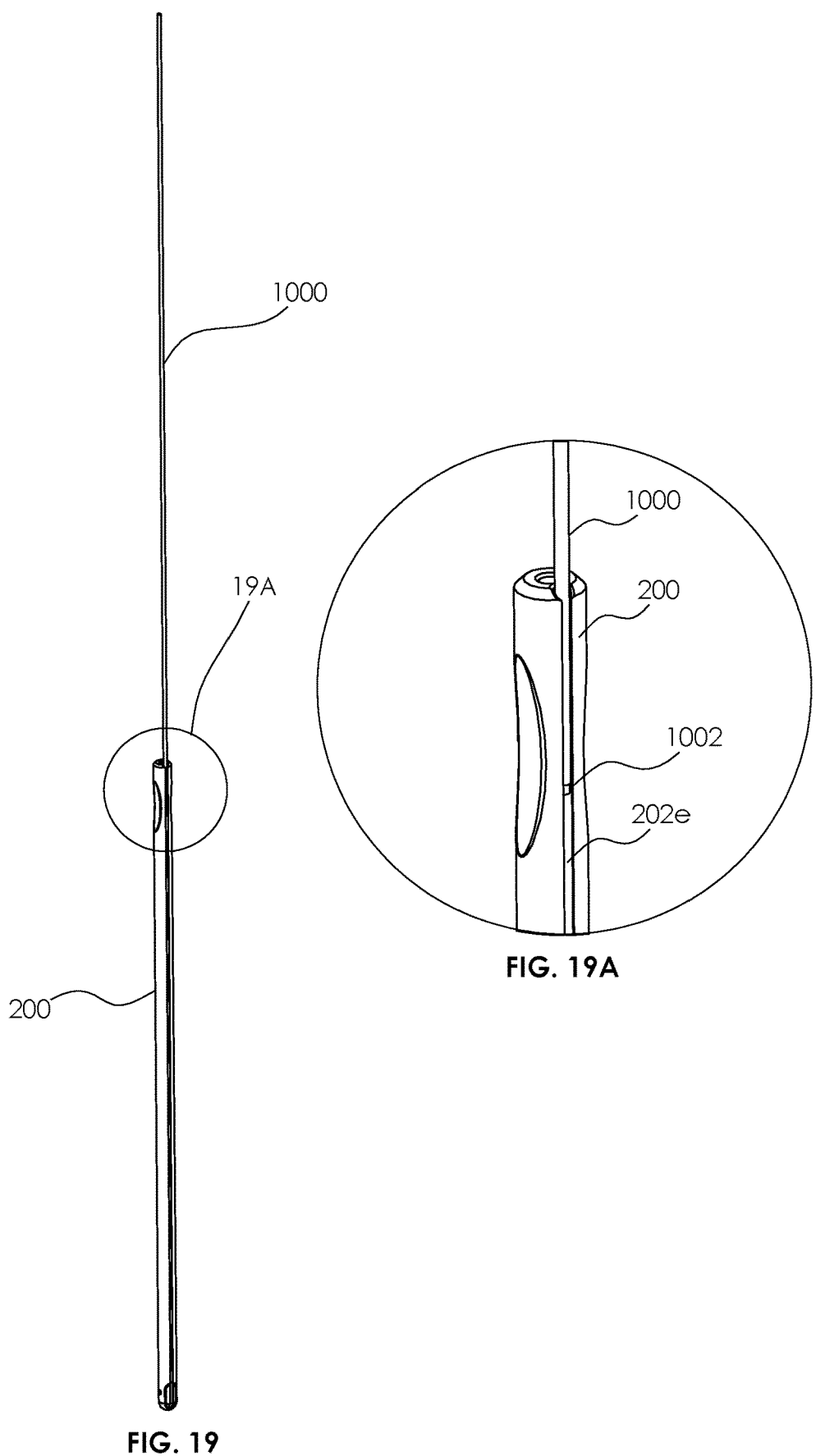
FIG. 19 is a perspective view of an inner cylindrical dilator of FIG. 12, illustrating use with a stimulation probe.
FIG. 19A is an enlarged view of the indicated area of detail of FIG. 19.
Figure 21A:
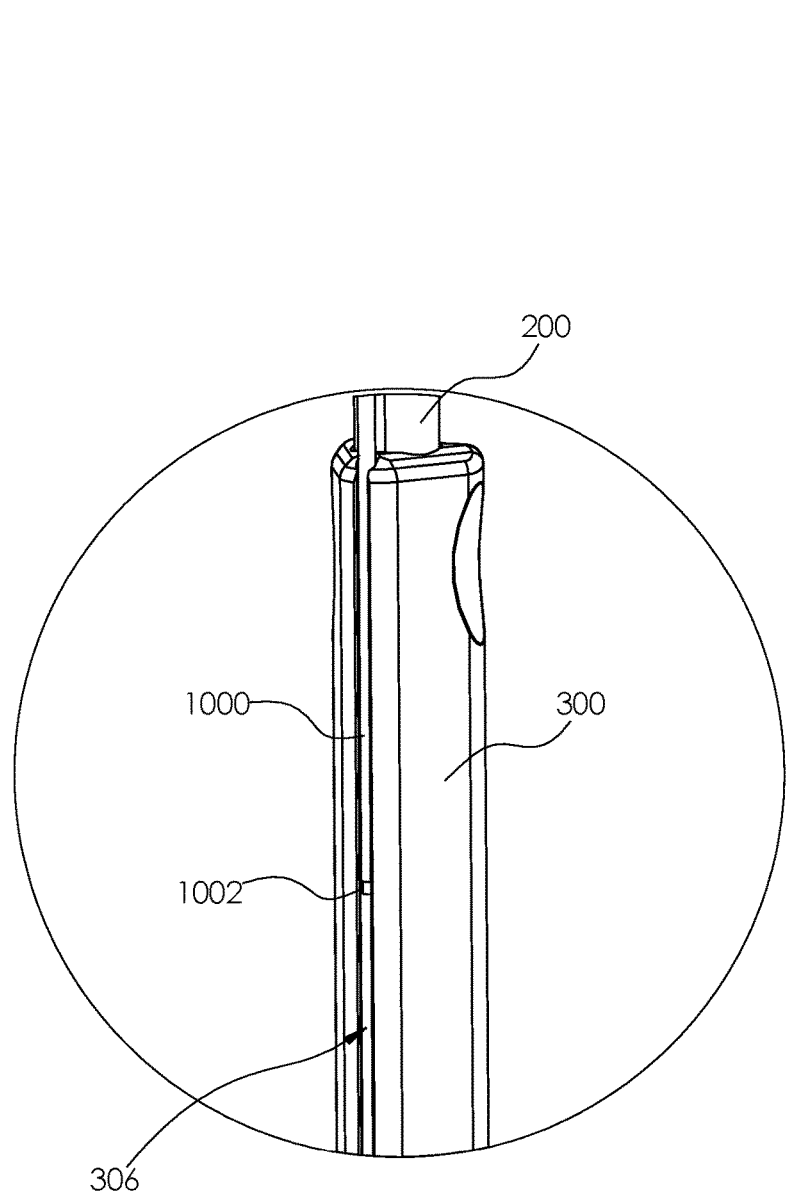
FIG. 21A is an enlarged view of the indicated area of detail of FIG. 21.
Figure 21:
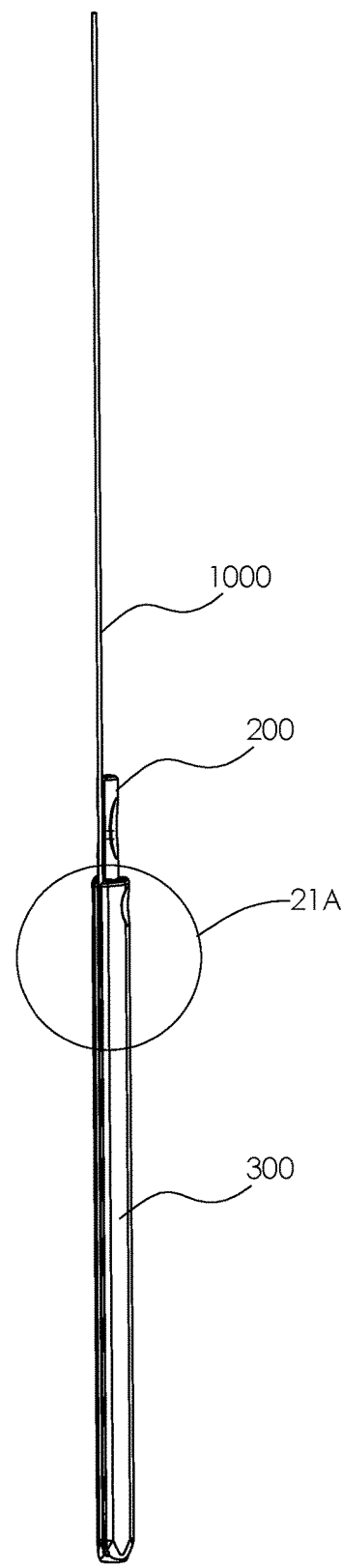
FIG. 21 is a perspective view of the dilator assembly of FIG. 11, illustrating use with the stimulation probe.

With reference now to FIGS. 8, 8A, 9, and 10, the first and second retractor blades 400a, 400b are identical and each includes a retractor blade body 402 having first and second rails 404, 406 that project from a planar inner surface 402a of retractor blade body 402 to engagement surfaces 404a, 406a of respective first and second rails 404, 406. The first and second rails 404, 406 taper inwardly toward one another and define cutouts 404b, 406b so that the first and second rails 404, 406 overhang a planar inner surface 402a to define an open longitudinal receiving trough 408 that is, e.g., c-shaped, for retaining a widening shim 700 (FIG. 16a) or lengthening shim 800 (FIG. 18). Engagement surfaces 404a, 406a are configured to complement the outer surface 303 of the outer triangular dilator 300 (FIGS. 11 and 13). The retractor blade body 402 further includes a stop 410 disposed in the open longitudinal receiving trough 408 adjacent a distal end portion of the retractor blade body 402 to limit distal movement of the widening shim 700 or the lengthening shim 800 relative to the retractor blade body 402. The first and second rails 404, 406 define notches 404c, 406c therein, respectively, which are disposed in registration with the open longitudinal receiving trough 408 proximal to the stop 410 for locking the widening or lengthening shims 700, 800 at a fixed depth relative to retractor blade body 402. The retractor blade body 402 also includes a mounting hook 412 supported on a proximal end thereof for securing the retractor blade body 402 to the first or second blade seats 124a, 134a (FIG. 2) of the respective first and second retractor arms 120, 130. It is contemplated that the posterior blade 500 and the first and second retractor blades 400a, 400b may be formed of, e.g., aluminum or a carbon fiber material. In a case of a carbon fiber material, the direction of layers of carbon fiber may be selected with respect to a particular structural component of the posterior blade 500, the first retractor blade 400a, or the second retractor blade 400b, in order to enhance structural integrity of the component and visualization of the orientation and position of the retractor relative to the patient when viewed under imaging such as fluoroscopy. For example, the direction of layers of carbon fiber may define an angle α in the range of about 80 degrees and about 100 degrees, and preferably about 70 degrees, with respect to a trailing edge 401 of the first or second retractor blades 400a, 400b. In addition, the posterior blade 500 and the first and second retractor blades 400a, 400b may be configured for interchangeable use. In other words, any of the blades may be attached interchangeably with any of the blade holders 124, 134, or the posterior blade holder assembly 116. In this manner, the surgeon advantageously may orient the retractor blades in the posterior, position relative to the operative site and patient anatomy, thereby providing maximum flexibility of use of the retractor and directions of motion of the blades during adjustment. In addition, it is contemplated that the various shims disclosed herein may be formed of titanium.

Figure 12:
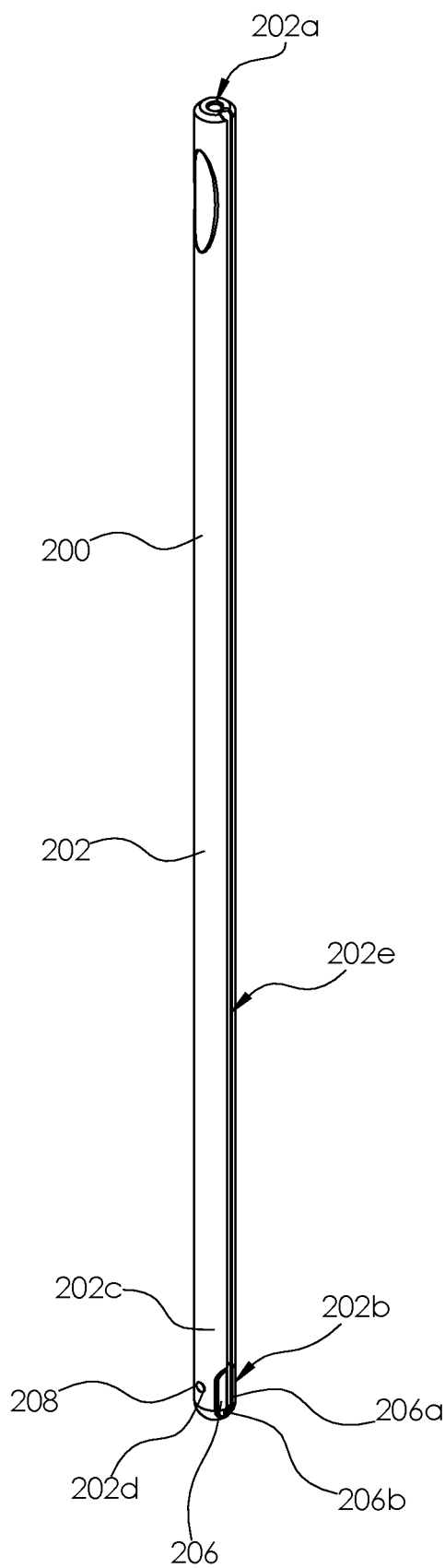
FIG. 12 is a perspective view of an inner cylindrical dilator of the dilator assembly of FIG. 11.

With reference to FIGS. 11-13, a dilator assembly 301 including an inner cylindrical dilator 200 and an outer triangular dilator 300 may be used in conjunction with the surgical retractor 100 during a surgical procedure. The inner cylindrical dilator 200 may include a cylindrical body 202 formed of a suitable biocompatible material such as, e.g., aluminum, that defines a circular cross-sectional outer profile. The inner cylindrical dilator 200 also defines a guidewire passage 202a that extends through a length of the cylindrical body 202 for receiving an intradiscal guidewire 900 therein. The cylindrical body 202 defines an insert window 202b through a sidewall 202c of cylindrical body 202 at a distal end portion of cylindrical body 202. The insert window 202b is positioned to receive an insert 206 of the inner cylindrical dilator 200 therethrough such that the cylindrical body 202 of inner cylindrical dilator 200 may support the insert 206 therein. The cylindrical body 202 further defines a pin hole 202d transverse to the insert window 202b for receiving a pin 208 of the inner cylindrical dilator 200 therein to pin the insert 206 to the cylindrical body 202. The cylindrical body 202 further includes an open side channel 202e that extends along a length of an outer surface of cylindrical body 202 into the insert window 202b. The insert 206 also includes an open side channel 206a that extends along an outer surface of the insert 206 and is disposed in registration with open side channel 202e of cylindrical body 202 while the insert 206 is pinned to cylindrical body 202. The open side channel 206a of the insert 206 extends to a distal abutment 206b that inhibits a stimulation probe 1000 (FIG. 20) from advancing distally beyond the distal abutment 206b (i.e., a depth or limit stop) when stimulation probe 1000 is selectively advanced along the open side channel 206a of the insert 206.

With particular reference to FIGS. 11 and 13, an outer triangular dilator 300 for use with the surgical retractor 100 has a triangular body 302 with an outer surface 303 having three planar outer sides 303a, 303b, 303c. For example, each planar side 303a, 303b, 303c of the triangular dilator 300 may be about 10 mm. However, when the triangular dilator 300 is rotated, a point where two of the planar sides 303a, 303b, 303c meet rotates in a circular path of about 14 mm. The triangular body 302 defines an inner dilator passage 304 longitudinally therethrough. The triangular body 302 further defines an open side channel 306 along the outer surface 303 of the triangular body 302 that extends to a distal abutment 306a (FIG. 22) that inhibits the stimulation probe 1000 (FIG. 22) from advancing distally beyond distal abutment 306a (i.e., a depth or limit stop) when stimulation probe 1000 is selectively advanced along open side channel 306. The triangular cross-sectional shape of the outer dilator advantageously requires a reduced cross-sectional area relative to a corresponding circular cross-section, thereby potentially reducing trauma to tissue and decreasing insertion force during insertion. The triangular shape also provides positive orientation of the retractor and the outer dilator during insertion.

With reference now to FIGS. 13a, 13b, 14a, 14b, and 15, the intradiscal shim 600 includes a shim body 602 that extends distally to a pointed tip 604 and includes a pair of flexible arms 606 that extend proximally from the shim body 602 and include nubs 606a that extend laterally therefrom for engaging the cutouts 504c, 506c of the posterior blade 500 to fix a position of the intradiscal shim 600 relative to posterior blade 500. The shim body 602 has planar front and rear surfaces and further includes a flexible finger 608 having an engagement tooth 608a projecting rearwardly therefrom. It is contemplated that the shim body 602 may define an opening 607 (FIGS. 13a and 13b) that may be used during an imaging process to indicate relative position of the shim body 602 with respect to the posterior blade 500. Thus, when the shim is fully deployed opening 607 will appear below the bottom edge of the blade when viewed under imaging.

Figure 8A:
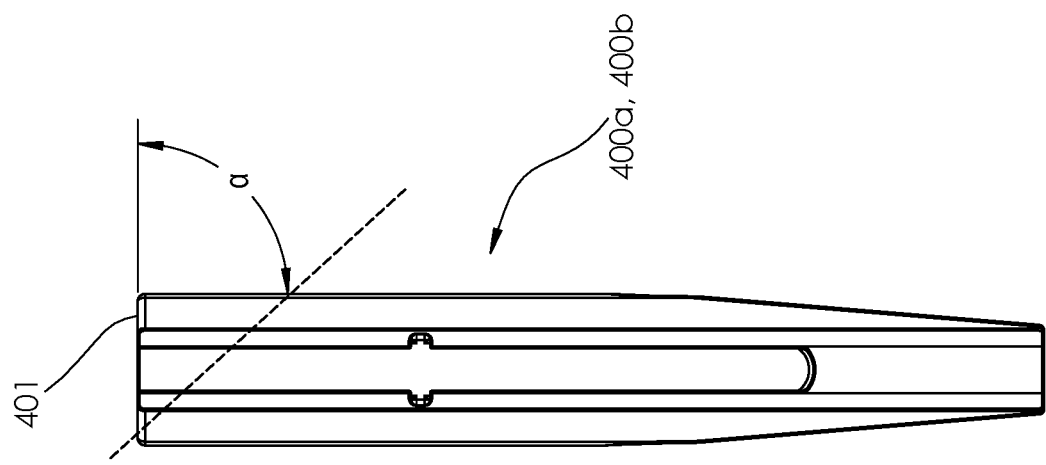
FIG. 8A is a side view of a first or second blade of FIG. 8, illustrating direction of layers of carbon fiber.
Figure 8:
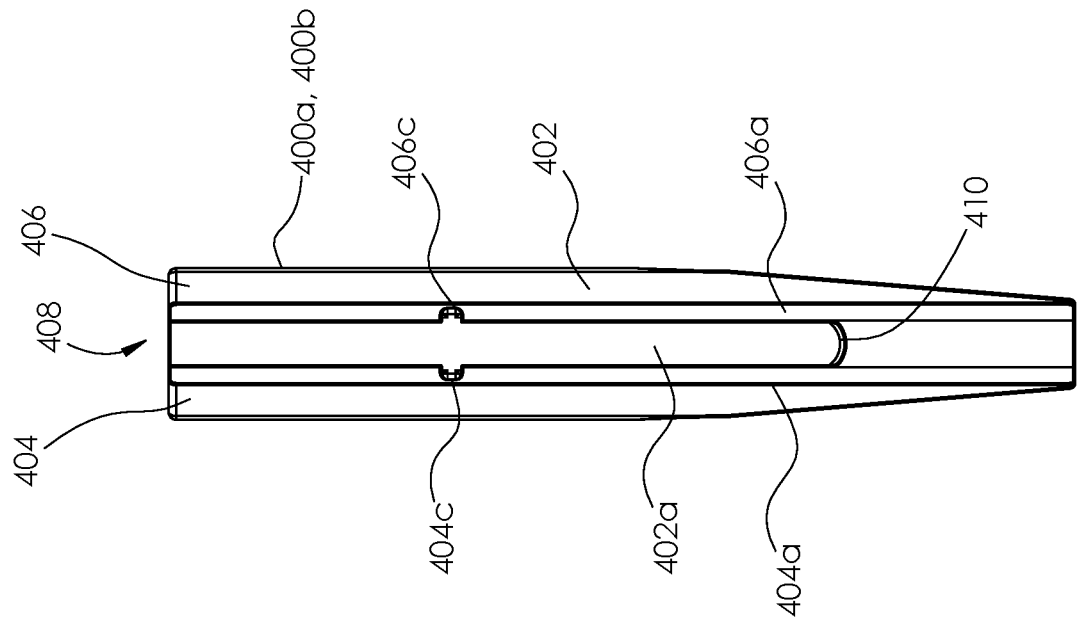
FIG. 8 is a front view of a first or second blade of the surgical retractor of FIG. 1.
Figure 10:
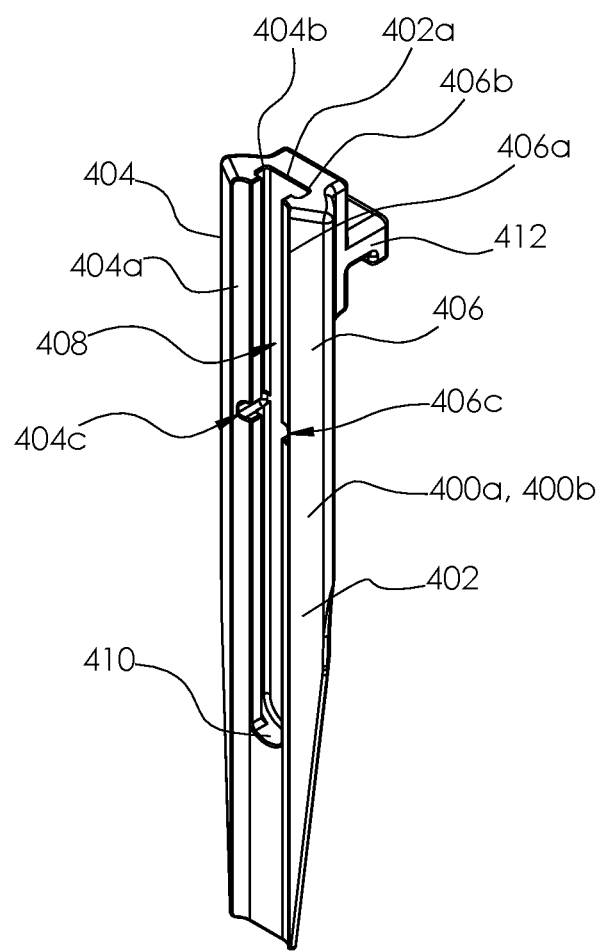
FIG. 10 is a perspective view of the first or second blade of FIG. 8.
Figure 16A:
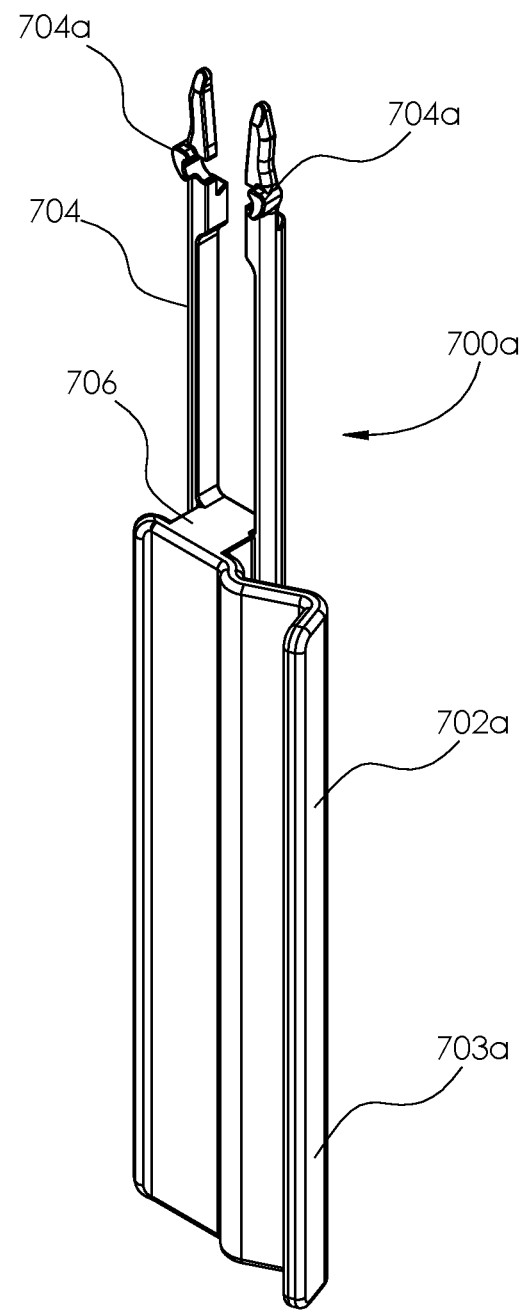
FIGS. 16a and 16b are perspective views of first and second widening shims, respectively, for use with the surgical retractor of FIG. 1.
Figure 16B:
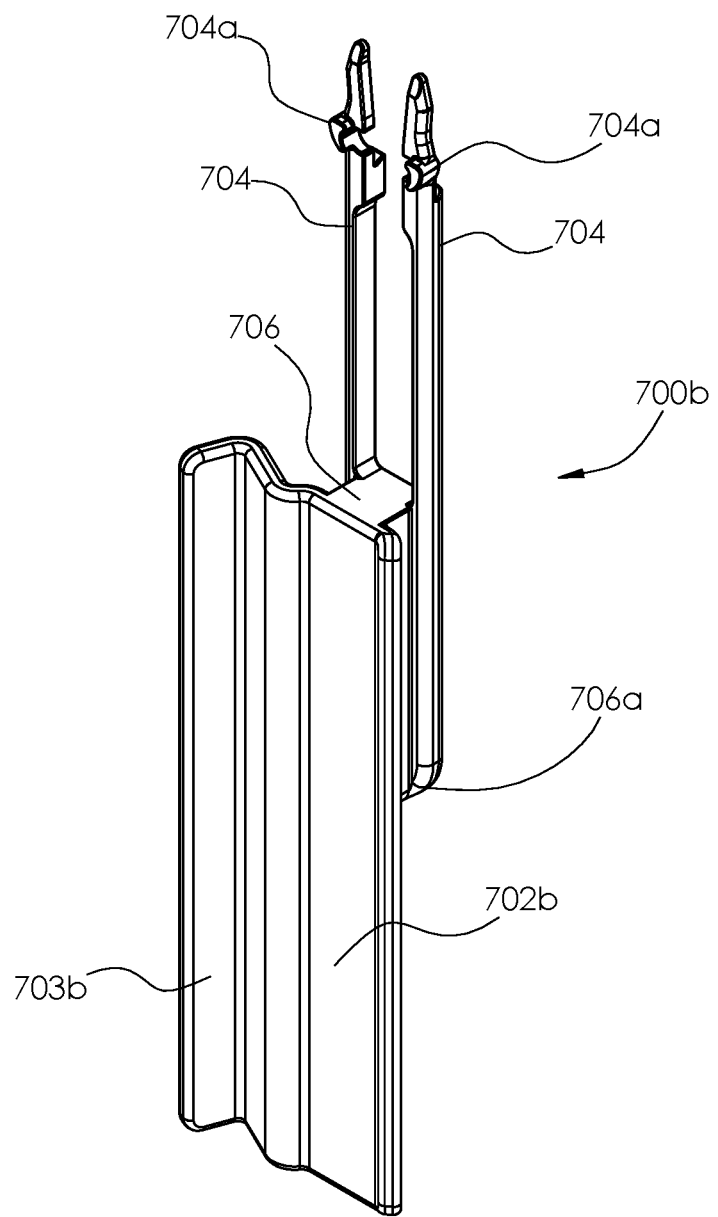

With reference to FIGS. 8, 16a, and 16b, widening shims 700a, 700b include widening bodies 702a, 702b with curvilinear profiles that mirror one another. For example, the widening body 702a has a lip 703a on a left side thereof and the widening body 702b has a lip 703b on a right side thereof. Each of the widening shims 700a, 700b further includes a pair of flexible arms 704 that extend proximally from a projection 706 that extends rearwardly from the respective widening bodies 702a, 702b. The projection 706 includes a nose 706a positioned to engage the stop 410 of the retractor blade body 402 of one of the first and second retractor blades 400a, 400b to limit distal movement of the respective widening shim 700a, 700b relative to retractor blade body 402 of one of the first and second retractor blades 400a, 400b. The flexible arms 704 include nubs 704a that are configured to secure the respective widening shims 700a, 700b to the notches 404c, 406c of the retractor blade body 402 for limiting insertion depth of the respective widening shims 700a, 700b relative to the retractor blade body 402. The widening shims 700a, 700b are usable with the first and second retractor blades 400a, 400b, but when supported by the first or second retractor blades 400a, 400b, the widening shims 700a, 700b do not extend past the distal ends of the respective first or second retractor blades 400a, 400b.

With reference now to FIGS. 8, 17a, 17b, and 18, a lengthening shim 800 may be used with the first and second retractor blades 400a, 400b. In particular, the lengthening shim 800 includes a lengthening body 802 with, e.g., a curvilinear profile, and an upper portion 802a and a lower portion 802b that are selectively movable relative to one another (in the direction of arrows "Z") in response to rotation of a lengthening screw 803 (in the direction of arrows "Y") threadably coupled to the upper and lower portions 802a, 802b. The upper portion 802a includes distally-extending legs 805 that are slidably received within leg lumens 807 defined in the lower portion 802b. The lengthening shim 800 further includes a pair of flexible arms 806 that extend proximally from a projection 808 that extends rearwardly from the lengthening body 802. The projection 808 includes a nose 808a that is positioned to engage the stop 410 of the retractor blade body 402 of one of the first and second retractor blades 400a, 400b to limit distal movement of the lengthening shim 800 relative to the retractor blade body 402 of one of the first and second retractor blades 400a, 400b. The flexible arms 806 are configured to secure the lengthening shim 800 to the notches 404c, 406c of retractor blade body 402 for limiting insertion depth of lengthening shim 800 relative to retractor blade body 402.

In use, a patient may be placed in a lateral decubitus position on a patient table. At this time, one or more skin incisions are made at the appropriate operative level so that subcutaneous tissue layers are taken down to expose the oblique fascia. The muscle fibers are separated as a finger is advanced into the retroperitoneal space. The peritoneum is safely released anteriorly as the retroperitoneal space is further developed. Finger palpation of the psoas muscle or the anterior tip of the transverse process is used to confirm proper location. Once verified, the inner cylindrical dilator 200 is introduced into the prepared path and advanced through the psoas muscle. Staying anterior to the lumbar plexus, the inner cylindrical dilator 200 is docked directly onto the disc. The intradiscal guidewire 900 is placed through the inner cylindrical dilator 200 and advanced into the disc, approximately halfway across the disc space as indicated through anteroposterior fluoroscopy. Additional soft tissue dilation is then performed with the outer triangular dilator 300 being advanced over the guidewire 900 and the inner cylindrical dilator 200 so that intradiscal guidewire 900 and the inner cylindrical dilator 200 are received through the inner dilator passage 304 of the outer triangular dilator 300 (FIG. 5). After an adequate path to the spine is prepared, blade length of the first and second retractor blades 400a, 400b, and the posterior blade 500 may be determined by markings located on the outer triangular dilator 300 in relation to the skin level. The first and second retractor blades 400a, 400b, and the posterior blade 500 are available from about 80 to about 180 mm in, e.g., 10 mm, increments.

With reference to FIGS. 19-22, if a surgeon elects to utilize neuromonitoring, open side channels 202e, 206a along the outer surfaces of the inner cylindrical dilator 200 and the insert 206 or open side channel 306 along the outer surface of triangular body 302, can be utilized to receive a stimulation probe 1000 for advancing stimulation probe 1000 relative to the inner cylindrical dilator 200 and the outer triangular dilator 300. When the stimulation probe 1000 is fully seated in inner cylindrical dilator 200, a distal tip 1002 of stimulation probe 1000 engages the distal abutment 206b. When the stimulation probe 1000 is fully seated in the outer triangular dilator 300, the distal tip 102 of the stimulation probe 1000 engages the distal abutment 306a.

Figure 15:
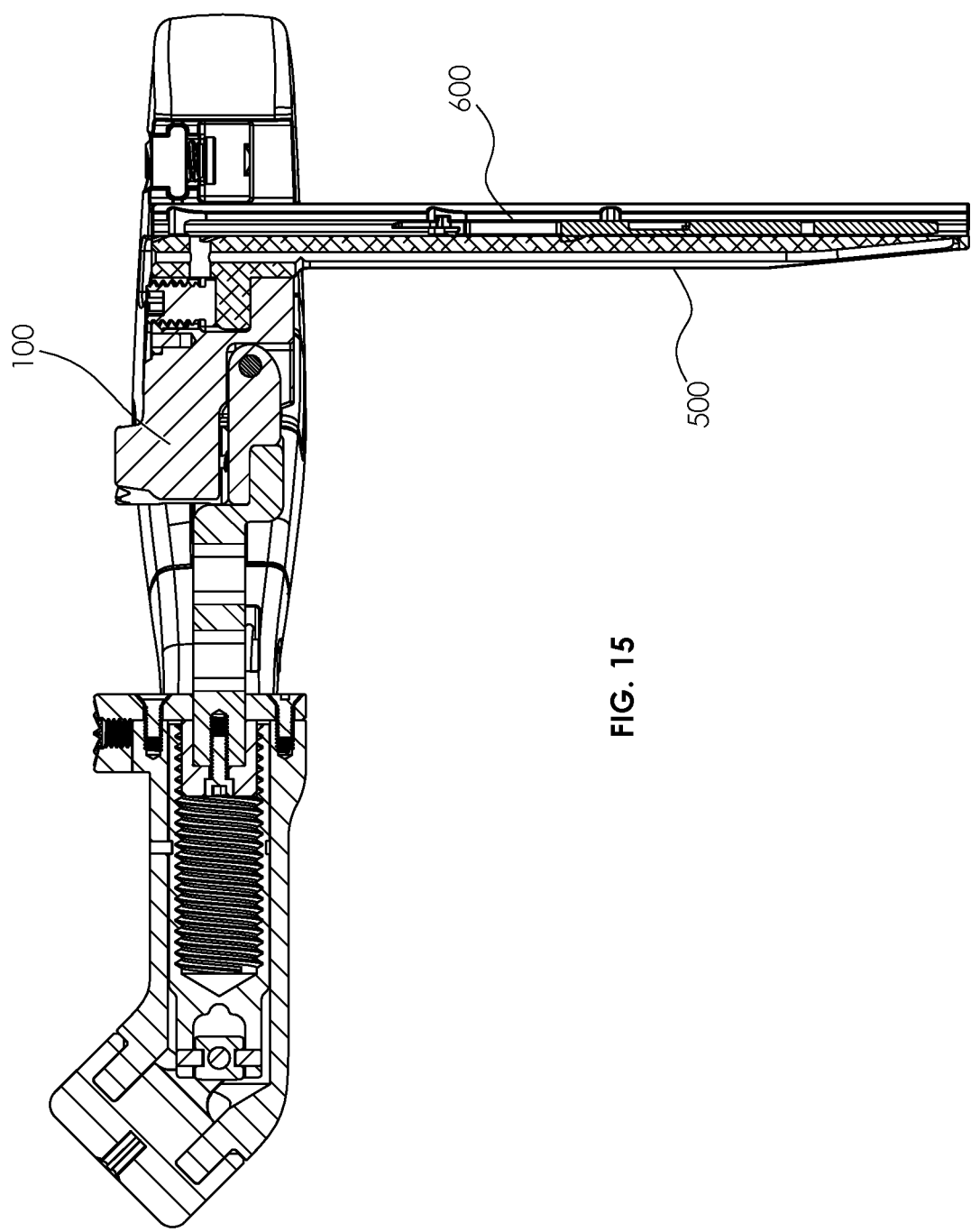

Once blade length is determined, the first and second retractor blades 400a, 400b, and the posterior blade 500 are mounted to the surgical retractor 100 and locked thereto via locking screws 116d, 124b, 134b of the surgical retractor 100. The surgeon may elect to use blades made of metal (e.g., aluminum) or a carbon fiber material and have such blades attached to the retractor blade holders. In particular, the first and second retractor blades 400a, 400b are mounted to the respective first and second retractor arms 120, 130. The posterior blade 500 is mounted to the posterior blade holder assembly 116. As pointed out above, however, different blade mounting orientations are permitted, if desired. If using the intradiscal shim 600, the intradiscal shim 600 is positioned within the open longitudinal receiving trough 508 of posterior blade 500 without being deployed past a distal end of posterior blade 500 prior to blade insertion into tissue (FIG. 15). Once the engagement tooth 608a of the intradiscal shim 600 is advanced through the open longitudinal receiving trough 508 past the recess 502b of the posterior blade 500, proximal movement of the intradiscal shim 600 causes the engagement tooth 608a to engage the recess 502b of the posterior blade 500 so that the intradiscal shim 600 cannot be removed from posterior blade 500 while the posterior blade 500 is secured to the retractor 100 as access to the recess 502b is only possible when the posterior blade 500 is removed from the retractor 100.

Figure 28:
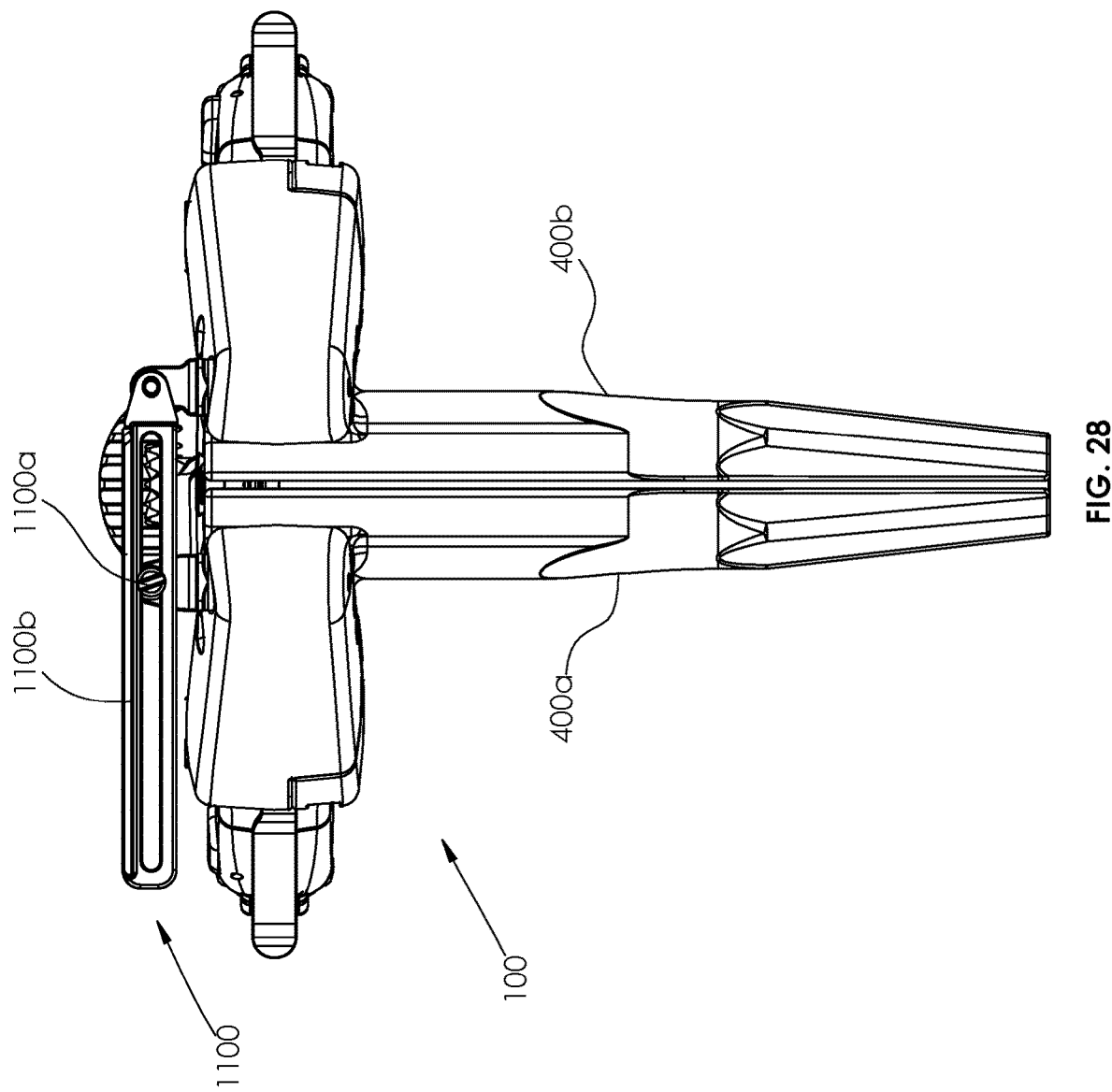
FIG. 28 is an end view of the surgical retractor of FIG. 1 with retractor blades in a first position.

The first and second retractor arms 120, 130 are pivoted about respective pivots "P1", "P2" to move the first and second retractor arms 120, 130 to be approximated about the outer surface 303 of the outer triangular dilator 300 so that first retractor blade 400a is spaced from second retractor blade 400b by, e.g., about 1 mm (FIG. 28). The first and second retractor arms 120, 130 may also be pivoted about respective pivots "P1", "P2" to move the first and second retractor arms 120, 130 from the approximated position to an open position as desired. The rotatable knob 114 is also rotated in a first direction to translate the posterior blade holder assembly 116 distally away from the tube assembly 110 of the surgical retractor 100 until the posterior blade 500 engages the outer triangular dilator 300 and is disposed in close approximation with the first and second retractor blades 400a, 400b so that the first and second retractor blades 400a, 400b, and the posterior blade 500 define a triangular opening around the outer triangular dilator 300. The triangular opening provides a reduced surface area compared to, e.g., a circular opening, which may reduce tissue trauma, as well as resistance to dilation during advancement. The rotatable knob 114 can also be rotated in a second direction to translate the posterior blade holder assembly 116 proximally toward the tube assembly 110 as desired.

Figure 23:
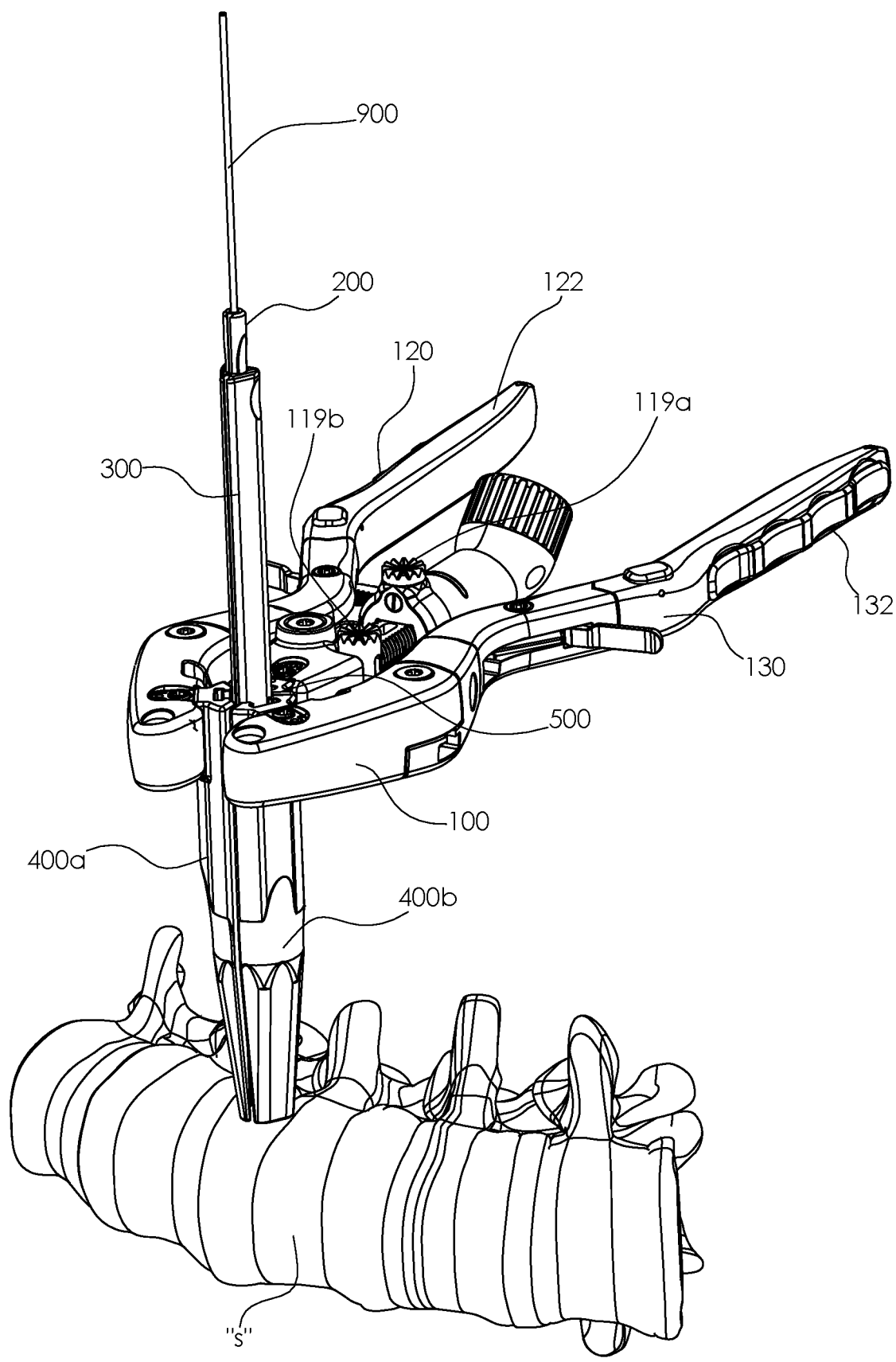
FIG. 23 is a perspective view of the surgical retractor of FIG. 1, illustrating use with the dilator assembly of FIG. 11.

With reference now to FIG. 23, the first and second retractor blades 400a, 400b, and the posterior blade 500 can then be advanced down the outer triangular dilator 300 into the tissue to engage the spine "S" with the first and second handle portions 122, 132 of the first and second retractor arms 120, 130 oriented toward the posterior aspect of the patient. Then, under fluoroscopy, the positioning of the first and retractor blades 400a, 400b, and the posterior blade 500 seated onto the disc space and properly aligned in lateral and anteroposterior views is verified. Use of carbon fiber materials may improve visualization of the orientation and position of the retractor relative to the patient when viewed under imaging such as fluoroscopy. The surgical retractor 100 can then be secured via first and/or second table mounts 119a, 119b using a table mount attachment (not shown).

Figure 13B:
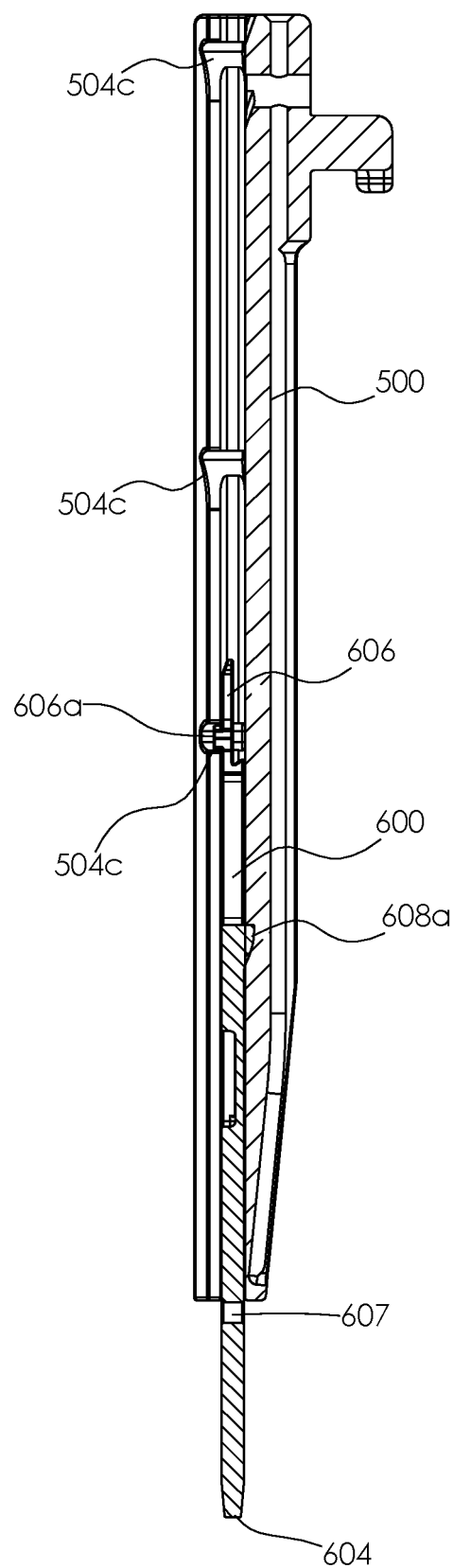

After the posterior blade 500 is determined to be positioned away from surrounding neurological structures, using a shim adjuster (not shown), the intradiscal shim 600 can be deployed relative to the posterior blade 500 into the disc space to a desired depth and secured to the posterior blade 500 via flexible arms 606 (FIG. 13b). Under imaging such as fluoroscopic imaging hole 607 will be visible beyond the tip of the blade when the shim is fully deployed.

Figure 29:
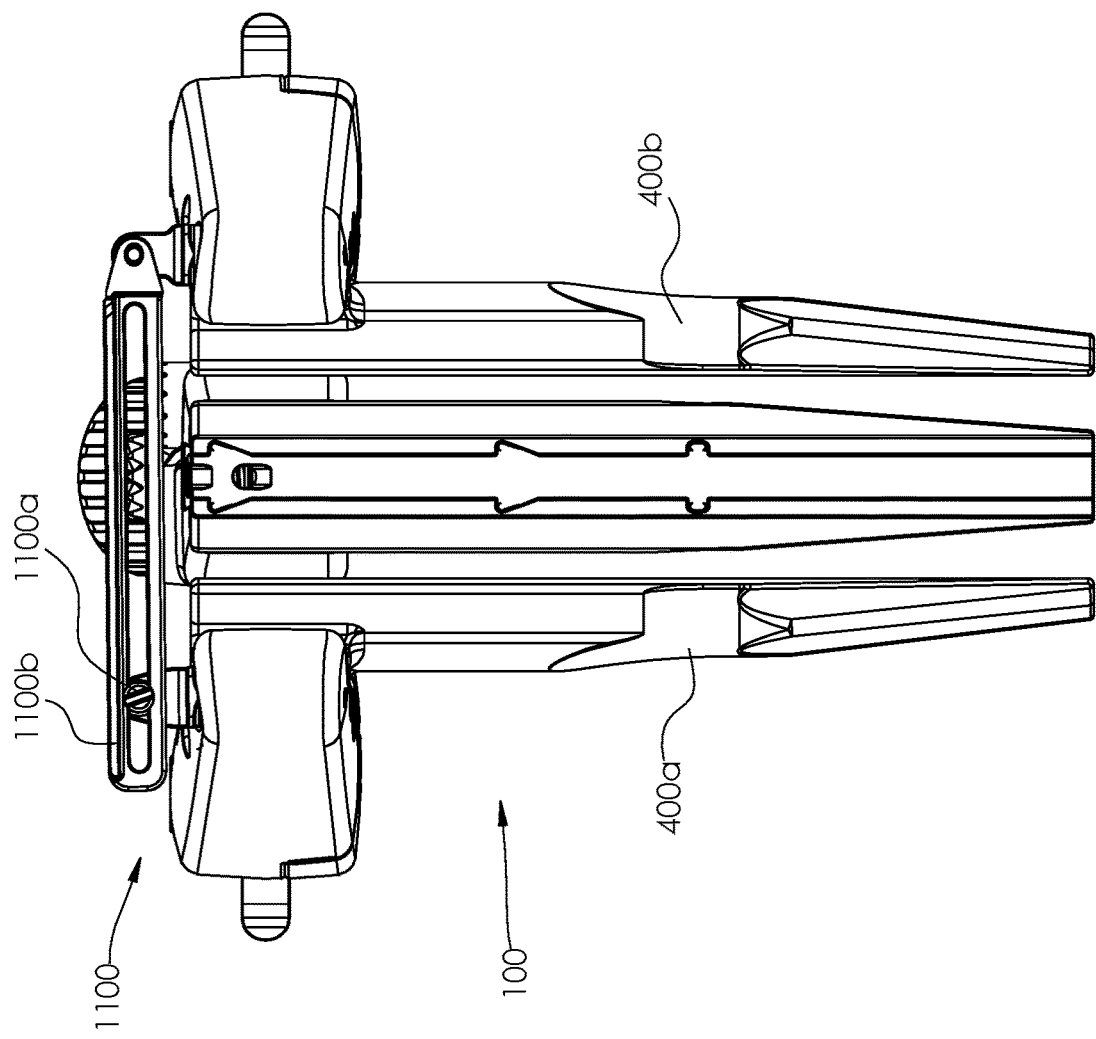
FIG. 29 is an end view of the surgical retractor of FIG. 28 with the retractor blades in a second position.
Figure 30:
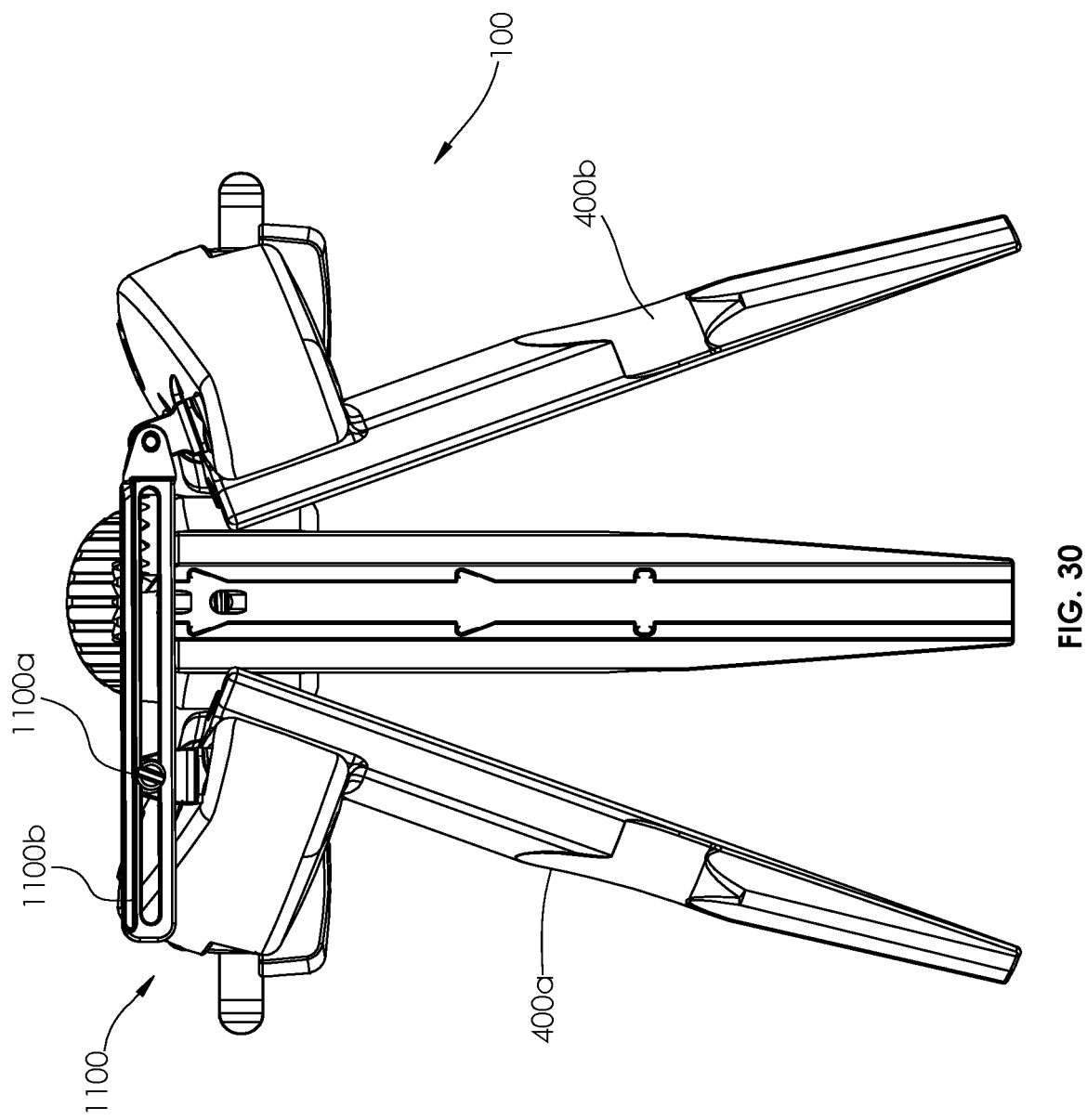
FIG. 30 is an end view of the surgical retractor of FIG. 28, with the retractor blades in the second position and angled with respect to arms of the retractor.

Each of the first and second retractor blades 400a, 400b, and posterior blade 500 can be independently manipulated to expand the operative corridor (FIG. 4). With reference to FIGS. 1-4, to move the first and second retractor arms 120, 130 away from one another, the first and second retractor arms 120, 130 can be pivoted about respective pivots "P1", "P2" by squeezing the first and second handle portions 122, 132 together or turning the first and/or second drive pins 122b, 132b of the respective first and second retractor arms 120, 130. The first and second retractor blades 400a, 400b can also be toed as desired via turning of first and/or second toeing screws 126, 136 of respective first and second retractor arms 120, 130 (FIG. 30). To move the posterior blade 500 away from the first and second retractor blades 400a, 400b and further expand the operative corridor, the posterior blade holder assembly 116 can be translated proximally toward tube assembly 110 by rotating the rotatable knob 114 (FIG. 29). Referring now to FIGS. 28-30, an anterior arm 1100 advantageously is designed and constructed to allow sliding movement of one end 1100a of the anterior arm 1100 relative to a cross-connecting arm portion 1100b. In this manner, the anterior arm 1100, with or without blade 1200 (FIG. 24) attached to the anterior arm 1100, may be permitted to lengthen or shorten during adjustment of the first and second retractor arms 120, 130. Thus, retractor arms 120, 130 may be adjusted relative to the spacing of the tips of the first and second retractor arms 120, 130 without having to remove the cross-connecting anterior arm 1100 or the anterior blade 1200. It is also contemplated that a locking mechanism may be provided to lock the anterior arm 1100 in position and prevent sliding adjustment of the arm when the locking mechanism is engaged.

Figure 24:
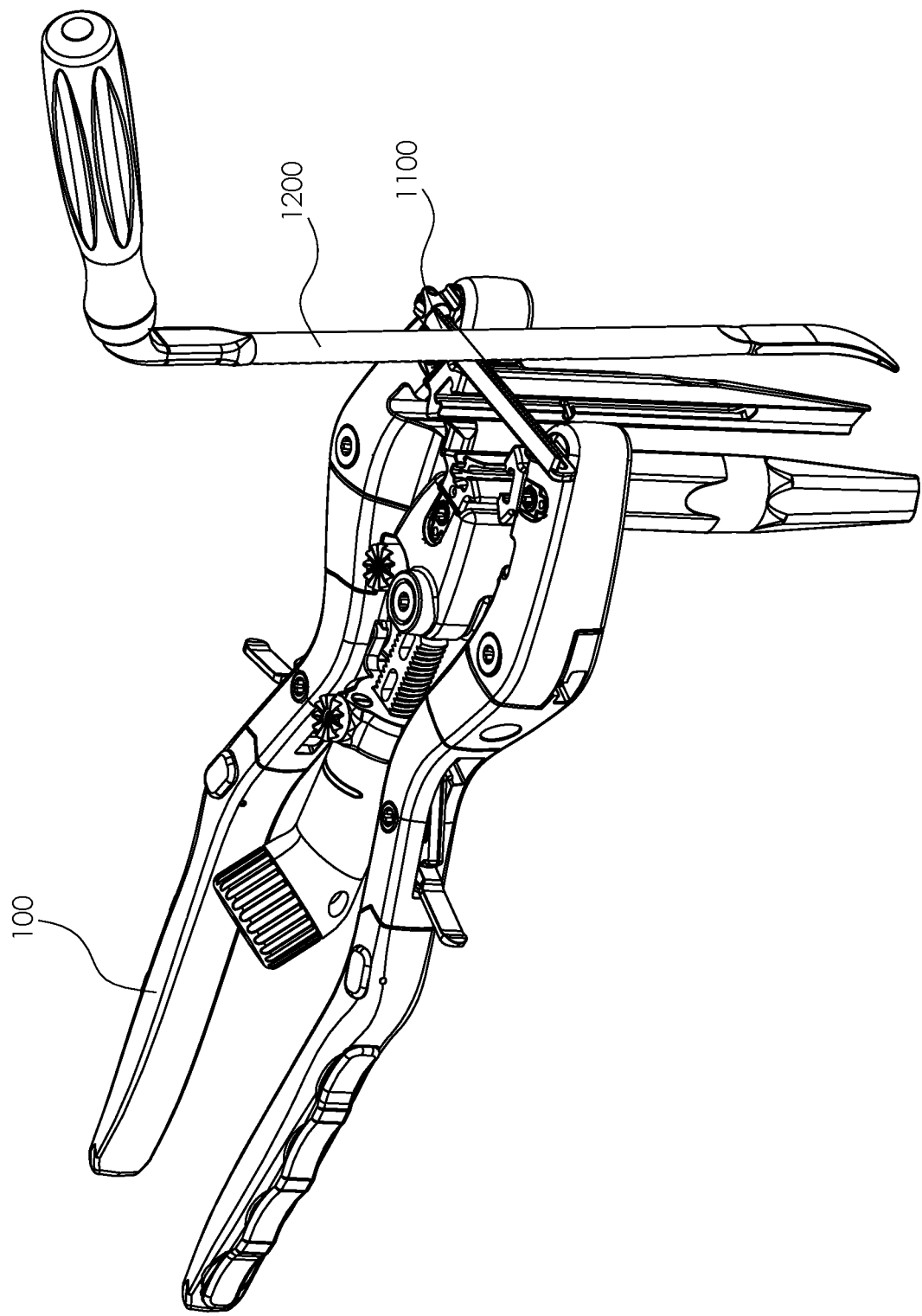
FIG. 24 is a perspective view of the surgical retractor of FIG. 1, illustrating use with an anterior arm.

Once the surgical retractor 100 is fixed in a desired position, the inner cylindrical dilator 200 and the outer triangular dilator 300 can be removed from the assembly to expose the operative site. A bifurcated reusable light source (not shown) can be utilized for lighting the operative corridor. If additional retraction is desired, an anterior arm 1100 and blade 1200 can be mounted to the retractor 100 as shown in FIG. 24.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical retractor comprising:
a body assembly including:
a body;
a rotatable knob disposed on the body;
first and second mounting wings extending from opposite sides of the body and each mounting wing defining an elongate opening extending therethrough and an edge having ratchet teeth;
first and second locking pawls positioned at the opposite sides of the body so as to releaseably engage the corresponding ratchet teeth;
a first blade holder operatively coupled with the rotatable knob such that rotation of the rotatable knob causes displacement of the first blade holder along a longitudinal axis of the first blade holder; and
a first blade detachably secured with the first blade holder, the first blade being configured for displacement with the first blade holder along the longitudinal axis and angulation relative to the first blade holder about a first toeing axis, the first toeing axis being defined by the first blade holder;
a first retractor arm coupled to the body by a first drive pin that extends through the first mounting wing opening and defining a first pivot axis about which the first retractor arm rotates, the first retractor arm including a second blade detachably secured thereto; and
a second retractor arm coupled to the body by a second drive pin that extends through the second mounting wing opening and defining a second pivot axis about which the second retractor arm rotates, the second retractor arm including a third blade detachably secured thereto;
wherein the second pivot axis is different from the first pivot axis, the first and second retractor arms being rotatable about the respective pivot axes between (i) a first configuration in which the second and third blades are proximate each other and (ii) a second configuration in which the second and third blades are spaced apart from each other such that the first and second arms are maintained at a distance corresponding to the second configuration when the first and second locking pawls releaseably engage the corresponding ratchet teeth,
wherein each of the first and second drive pins is adjustable within the wing openings of respective mounting wings to change the distance between the respective first and second drive pins in response to the rotation of the first and second retractor arms, and
wherein the second and third blades are configured to angulate about respective second and third toeing axes that are defined by the respective first and second retractor arms.

2. The surgical retractor according to claim 1, wherein at least a portion of the first or second retractor arms is made of a carbon fiber material.

3. The surgical retractor according to claim 1, wherein at least a portion of the first blade, second blade or third blade is made of a carbon fiber material.

4. The surgical retractor according to claim 1, wherein at least a portion of the first blade, second blade or third blade is made of metal.

5. The surgical retractor according to claim 1, wherein the first blade holder is configured to secure the first blade thereto by a locking screw.

6. The surgical retractor according to claim 1, wherein the first blade is configured for axial displacement independent of the angulation thereof.

7. The surgical retractor according to claim 1, wherein the first blade is configured to angulate about the first toeing axis orthogonal to the longitudinal axis defined by the first blade holder.

8. The surgical retractor according to claim 1, wherein the first or second retractor arm includes a handle portion, an arm toeing base, and a blade holder configured to secure the corresponding second or third blade thereto, the blade holder coupled to the arm toeing base by a toeing screw that is rotatable to enable the blade holder to rotate relative to the arm toeing base.

9. The surgical retractor according to claim 8, wherein at least a portion of the arm toeing base is made of a carbon fiber material.

10. The surgical retractor according to claim 8, wherein at least a portion of the blade holder is made of a carbon fiber material.

11. The surgical retractor according to claim 1, wherein the first, second, and third blades are configured to define a cavity when proximate each other.

12. The surgical retractor according to claim 11, wherein the cavity has a triangular shape.

13. The surgical retractor according to claim 1, wherein the first blade is configured to support an intradiscal shim.

14. The surgical retractor according to claim 13, wherein the first blade is configured to lock a relative position of the intradiscal shim thereto.

15. The surgical retractor according to claim 1, wherein when the first and second retractor arms are in the approximated configuration, the second and third blades define a gap of about 1 mm.

* * * * *